US012733971B2

(12) United States Patent
Ren et al.

(10) Patent No.: US 12,733,971 B2
(45) Date of Patent: Sep. 15, 2026

(54) INTEGRATED SURGICAL SYSTEM

(71) Applicants: WUHAN MINDRAY SCIENTIFIC CO., LTD., Wuhan City (CN); SHENZHEN MINDRAY BIO-MEDICAL ELECTRONICS CO., LTD., Shenzhen (CN)

(72) Inventors: Jian Ren, Shenzhen (CN); Ronghui Lian, Shenzhen (CN); Canwu Zhong, Shenzhen (CN); Jianhua Huang, Shenzhen (CN); Pengfei Zuo, Shenzhen (CN); Jian Cen, Shenzhen (CN)

(73) Assignees: Wuhan Mindray Scientific Co., Ltd., Wuhan (CN); Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 155 days.

(21) Appl. No.: 18/759,472

(22) Filed: Jun. 28, 2024

(65) Prior Publication Data

US 2024/0350189 A1 Oct. 24, 2024

Related U.S. Application Data

(63) Continuation of application No. PCT/CN2022/136005, filed on Dec. 1, 2022.

(30) Foreign Application Priority Data

Dec. 31, 2021 (CN) ......................... 202111659666.4

(51) Int. Cl.

| | |
|---|---|
| ***A61B 18/12*** | (2006.01) |
| ***A61B 18/14*** | (2006.01) |
| *A61B 18/00* | (2006.01) |

(52) U.S. Cl.
CPC .......... *A61B 18/1206* (2013.01); *A61B 18/14* (2013.01); *A61B 2018/00601* (2013.01);
(Continued)

(58) Field of Classification Search
CPC . A61B 18/1206; A61B 18/14; A61B 18/1445; A61B 2018/00601;
(Continued)

(56) References Cited

U.S. PATENT DOCUMENTS

| | | | | |
|---|---|---|---|---|
| 11,304,741 | B2 * | 4/2022 | Leuck | A61B 18/00 |
| 2017/0086876 | A1 * | 3/2017 | Wiener | A61B 18/1445 |

(Continued)

FOREIGN PATENT DOCUMENTS

| | | | |
|---|---|---|---|
| CN | 101849839 | A | 10/2010 |
| CN | 210170159 | U | 3/2020 |

(Continued)

OTHER PUBLICATIONS

Extended European Search Report dated Mar. 25, 2025, issued in related European Patent Application No. 22914010.8 (13 pages).

(Continued)

*Primary Examiner* — Michael F Peffley
(74) *Attorney, Agent, or Firm* — Sheppard Mullin Richter & Hampton LLP

(57) ABSTRACT

An integrated surgical system includes a voltage conversion unit, a first and a second power amplifier unit, an isolation conversion unit, an operation and driving unit, output ports for an electrosurgical knife and an ultrasonic knife. The first power amplifier unit converts a DC voltage into an AC voltage and amplifies the AC voltage; the isolation conversion unit isolates and converts the AC voltage outputted by the first power amplifier unit, and provides the AC voltage to the output port for the electrosurgical knife; the second power amplifier unit receives power from the voltage con- (Continued)

version unit, and amplifies a third signal; the isolation conversion unit isolates and converts an output of the second power amplifier unit, and provides the output to the output port for the ultrasonic knife. The integrated surgical system integrates an electrosurgical knife function and an ultrasonic knife function in a device system.

20 Claims, 12 Drawing Sheets

(52) U.S. Cl.
CPC ............... *A61B 2018/00702* (2013.01); *A61B 2018/00994* (2013.01); *A61B 2018/124* (2013.01); *A61B 2018/1253* (2013.01); *A61B 2018/126* (2013.01)

(58) Field of Classification Search
CPC ........... A61B 2018/00607; A61B 2018/00702; A61B 2018/00892; A61B 2018/00994; A61B 2018/124; A61B 2018/1253; A61B 2018/126
See application file for complete search history.

(56) References Cited

U.S. PATENT DOCUMENTS

| | | | | |
|---|---|---|---|---|
| 2018/0042659 | A1* | 2/2018 | Rupp ............. | A61B 17/320092 |
| 2019/0201043 | A1* | 7/2019 | Shelton, IV ....... | A61B 18/1445 |

FOREIGN PATENT DOCUMENTS

| | | | |
|---|---|---|---|
| CN | 213552294 | U | 6/2021 |
| CN | 113397656 | A | 9/2021 |
| CN | 115281787 | A | 11/2022 |
| EP | 3892217 | A1 | 10/2021 |
| WO | 2017/058618 | A1 | 4/2017 |

OTHER PUBLICATIONS

PCT International Search Report and the Written Opinion mailed Feb. 21, 2023, issued in related International Application No. PCT/CN2022/136005, with partial English translation (13 pages).

* cited by examiner

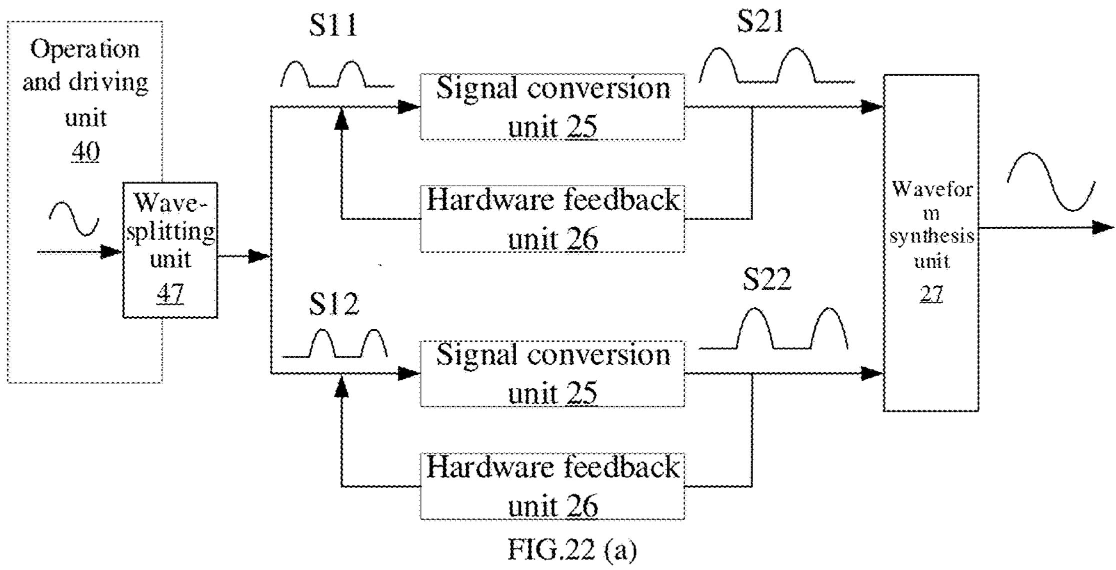
FIG.22 (a)
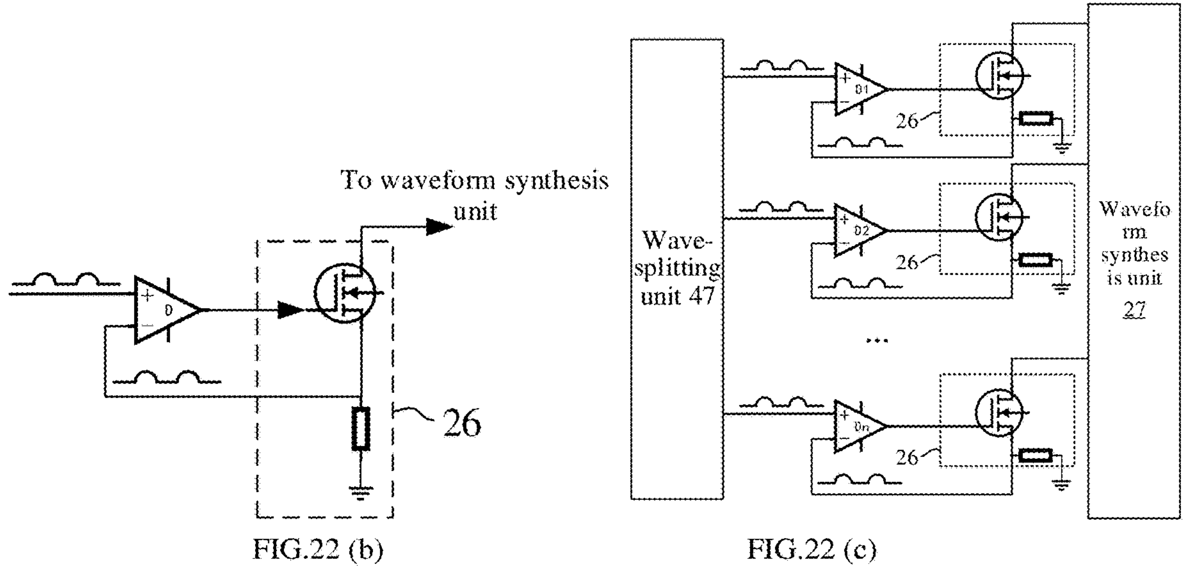
FIG.22 (b)
FIG.22 (c)

INTEGRATED SURGICAL SYSTEM

CROSS-REFERENCE TO RELATED APPLICATIONS

This application is a continuation application of International Patent Application No. PCT/CN2022/136005, filed on Dec. 1, 2022, which is based on and claims priority to and benefits of Chinese Patent Application No. 202111659666.4, filed on Dec. 31, 2021. The entire content of all of the above-referenced applications is incorporated herein by reference.

TECHNICAL FIELD

The disclosure relates to a technical field of medical devices, and more particularly to an integrated surgical system.

BACKGROUND

An energy system for high-frequency electrosurgical knife and an energy system for an ultrasonic knife have been widely used in clinical surgery. A high-frequency electrosurgical knife utilizes heat effect generated by a high-frequency current passing through human tissue to realize cutting, staunching and solidification of the tissue. The ultrasonic knife utilizes an ultrasonic mechanical vibration of a mechanical knife head to realize cutting, staunching and solidification of tissue. Usually, an output power range of the high-frequency electrosurgical knife is large, and the high-frequency electrosurgical knife is high in efficiency during skin and tissue cutting, but has a large range of thermal damage generated around cut tissue and is not suitable for fine surgical operation. The output energy of the ultrasonic knife is relatively small, and the damage to surrounding tissue of a surgical site is much smaller than that of the electrosurgical knife, which can be safely used for separating and cutting beside important large blood vessels. These two energy systems have respective disadvantages, and are generally used at the same time in a same procedure, so as to cooperate with each other to achieve efficient and smooth operation.

The energy system for high-frequency electrosurgical knife and the energy system for ultrasonic knife are usually two independent devices in a surgical room, and if the energy system for high-frequency electrosurgical knife and the energy system for ultrasonic knife need to be used simultaneously in a surgical operation, it is necessary to arrange the two devices at a periphery of a surgical table at the same time. When the two energy systems are used by a doctor, different devices are also frequency switched to switch energy output, which brings inconvenience to the surgical operation, and may cause use confusion in a severe case and result in a surgical risk. Moreover, a space of the surgical room is usually not large, except that many other devices need to be arranged at the same time besides the energy system, the arrangement of the two energy systems occupies more surgical room space, which brings inconvenient for the management of the surgical room.

SUMMARY

In order to solve above problems, this disclosure discloses an integrated surgical system, which is described in detail below.

According to a first aspect, an embodiment provides an integrated surgical system, including a voltage conversion unit, a full-bridge power amplifier circuit, a linear power amplifier circuit, a first isolation conversion unit, a second isolation conversion unit, an operation and driving unit, a user input unit, a sampling unit, an output port for an electrosurgical knife, and an output port for an ultrasonic knife;

- the output port for the electrosurgical knife is configured to deliver energy to the electrosurgical knife; the output port for the ultrasonic knife is configured to deliver energy to the ultrasonic knife;
- the voltage conversion unit is configured to convert an input voltage into a DC voltage which drives the full-bridge power amplifier circuit or into a DC voltage which is delivered to the linear power amplifier circuit, according to a first control signal;
- the full-bridge power amplifier circuit is configured to convert the DC voltage, which is outputted by the voltage conversion unit, into an AC voltage, according to a second control signal; wherein the first isolation conversion unit is configured to filter the AC voltage into a sine-wave voltage, perform resonance, isolation and conversion on the sine-wave voltage, and then deliver the sine-wave voltage to the output port for the electrosurgical knife for delivering energy to the electrosurgical knife;
- the linear power amplifier circuit is configured to receive the DC voltage delivered from the voltage conversion unit, and convert a third signal into a sine-wave signal, wherein the third signal includes two paths of a driving current signal; the second isolation conversion unit is configured to perform isolation and conversion on the sine-wave signal, and then deliver the sine-wave signal to the output port for the ultrasonic knife for delivering energy to the ultrasonic knife;
- the sampling unit is configured to sample an input or an output of the first isolation conversion unit, so as to obtain a first sampled electrical signal; the sampling unit is further configured to sample an input or an output of the second isolation conversion, so as to obtain a second sampled electrical signal;
- the user input unit is configured to receive a control parameter, which is inputted by a user;
- the operation and driving unit is configured to generate the first control signal, the second control signal, and the third signal, according to the control parameter; wherein the operation and driving unit is further configured to adjust the first control signal and/or the second control signal according to the first sampled electrical signal, and to adjust the third signal according to the second sampled electrical signal.

According to a second aspect, an embodiment provides an integrated surgical system, including a voltage conversion unit, a first power amplifier unit, a second power amplifier unit, an isolation conversion unit, an operation and driving unit, an output port for an electrosurgical knife, and an output port for an ultrasonic knife;

- the output port for the electrosurgical knife is configured to deliver energy to the electrosurgical knife; the output port for the ultrasonic knife is configured to deliver energy to the ultrasonic knife;
- the voltage conversion unit is configured to convert an input voltage into a DC voltage which drives the first power amplifier unit or into a DC voltage which is delivered to the second power amplifier unit, according to a first control signal;

the first power amplifier unit is configured to convert the DC voltage, which is outputted by the voltage conversion unit, into an AC voltage, and amplify the AC voltage, according to a second control signal; wherein the isolation conversion unit is configured to perform isolation and conversion on the amplified AC voltage, which is outputted by the first power amplifier unit, and then deliver the amplified AC voltage to the output port for the electrosurgical knife for delivering energy to the electrosurgical knife;

the second power amplifier unit is configured to receive the DC voltage delivered from the voltage conversion unit, amplify a third signal and output the amplified third signal; wherein the isolation conversion unit is further configured to perform isolation and conversion on an output of the second power amplifier unit, and then deliver said output to the output port for the ultrasonic knife for delivering energy to the ultrasonic knife;

the operation and driving unit is configured to generate the first control signal, the second control signal, and the third signal.

In an embodiment, the isolation conversion unit includes a first isolation conversion unit and a second isolation conversion unit; the first isolation conversion unit is configured to perform insolation and conversion on an output of the first power amplification unit, and then deliver said output to the output port for the electrosurgical knife;

the second isolation conversion unit is configured to perform isolation and conversion on the output of the second power amplifier unit, and then deliver said output to the output port for the ultrasonic knife;

the integrated surgical system further includes a sampling unit; wherein the sampling unit is configured to sample an input or an output of the first isolation conversion unit, so as to obtain a first sampled electrical signal; the sampling unit is further configured to sample an input or an output of the second isolation conversion, so as to obtain a second sampled electrical signal;

the operation and driving unit is further configured to adjust the first control signal and/or the second control signal according to the first sampled electrical signal, and to adjust the third signal according to the second sampled electrical signal.

In an embodiment, the first sampled electrical signal includes at least one of a voltage, a current, and power, and the second sampled electrical signal includes at least one of a voltage, a current, and power.

In an embodiment, the isolation conversion unit includes a first isolation conversion unit, which is configured to perform insolation and conversion on an output of the first power amplification unit, and then deliver said output to the output port for the electrosurgical knife; wherein the first isolation conversion unit includes at least one of a series-parallel resonant circuit, a common-mode filter circuit, and a turning-off absorption circuit;

the series-parallel resonant circuit is configured to filter the output of the first power amplifier unit;

the common-mode filter circuit is configured to filter a common-mode signal out of the output of the first power amplifier unit;

the turning-off absorption circuit is configured to absorb oscillation after the first power amplifier unit is turned off.

In an embodiment, the first power amplifier unit is a full-bridge power amplifier circuit.

In an embodiment, an LC series circuit is connected between two output terminals of the full-bridge power amplifier circuit.

In an embodiment, the integrated surgical system further includes an impedance matching circuit, which is connected between the second power amplifier unit and the isolation conversion unit, and configured to perform impedance matching.

In an embodiment, the second power amplifier unit is a linear power amplifier circuit.

In an embodiment, the operation and driving unit includes a processor, a waveform generator, a digital-to-analog conversion unit and a wave-splitting unit;

the processor is configured to generate the first control signal;

the processor is further configured to control the waveform generator to generate a second digital signal waveform as the second control signal;

the processor is further configured to control the waveform generator to generate a third digital signal waveform; the digital-to-analog conversion unit is configured to convert the third digital signal waveform into a third analog signal waveform, and the wave-splitting unit is configured to wave-split the third analog signal waveform to obtain the third signal.

In an embodiment, the integrated surgical system further includes a user input unit, which is configured to receive a control parameter, which is inputted by a user; the operation and driving unit is further configured to generate at least one of the first control signal, the second control signal, and the third signal, at least according to the control parameter.

In an embodiment, the output port for the electrosurgical knife includes a mono-pole terminal, a neutral-pole terminal, and a bi-pole terminal.

In an embodiment, the integrated surgical system further includes a switch component, wherein the switch component includes a first group of switches and a second group of switches; wherein the first group of switches are configured to connect and disconnect an energy delivery from the isolation conversion unit to the output port for the electrosurgical knife; and the second group of switches are configured to connect and disconnect an energy delivery from the isolation conversion unit to the output port for the ultrasonic knife.

In an embodiment, the output port for the electrosurgical knife and the output port for the ultrasonic knife share a same mechanical insertion port; wherein when a surgical instrument is inserted into the mechanical insertion port, the operation and driving unit is further configured to identify a type of the inserted surgical instrument through the mechanical insertion port; wherein the surgical instrument at least includes two types, one type is ultrasonic knife, and the other type is electrosurgical knife; wherein the surgical instrument is provided with a trigger key;

the operation and driving unit is further configured to control the first group of switches to be switched on, so as to deliver energy to the electrosurgical knife through the voltage conversion unit, the first power amplification unit and the isolation conversion unit, when the trigger key is triggered; if the type of the surgical instrument is currently identified as electrosurgical knife;

the operation and driving unit is further configured to control the second group of switches to be switched on, so as to deliver energy to the ultrasonic knife through the voltage conversion unit, the second power amplification unit and the isolation conversion unit, when the trigger key is triggered; if the type of the surgical instrument is currently identified as ultrasonic knife.

In an embodiment, the type of the electrosurgical knife includes at least three types, the first type is mono-pole electrosurgical knife, the second type is neutral-pole electrosurgical knife, and the third type is bi-pole electrosurgical knife; the first group of switches include a first group of sub-switches, a second group of sub-switches, and a third group of sub-switches; the first group of sub-switches are configured to connect and disconnect an energy delivery from the isolation conversion unit to the mono-pole terminal; the second group of sub-switches are configured to connect and disconnect an energy delivery from the isolation conversion unit to the neutral-pole terminal; the third group of sub-switches are configured to connect and disconnect an energy delivery from the isolation conversion unit to the bi-pole terminal;

in order to control the first group of switches to be switched on, so as to deliver energy to the electrosurgical knife through the voltage conversion unit, the first power amplification unit and the isolation conversion unit, when the trigger key is triggered; if the type of the surgical instrument is currently identified as electrosurgical knife; the operation and driving unit is further configured to:

control the first group of sub-switches to be switched on, so as to deliver energy to the mono-pole electrosurgical knife through the voltage conversion unit, the first power amplification unit and the isolation conversion unit, when the trigger key is triggered; if the type of the surgical instrument is currently identified as mono-pole electrosurgical knife;

control the second group of sub-switches to be switched on, so as to deliver energy to the neutral-pole electrosurgical knife through the voltage conversion unit, the first power amplification unit and the isolation conversion unit, when the trigger key is triggered; if the type of the surgical instrument is currently identified as neutral-pole electrosurgical knife;

control the third group of sub-switches to be switched on, so as to deliver energy to the bi-pole electrosurgical knife through the voltage conversion unit, the first power amplification unit and the isolation conversion unit, when the trigger key is triggered; if the type of the surgical instrument is currently identified as bi-pole electrosurgical knife.

In an embodiment, the output port for the electrosurgical knife and the output port for the ultrasonic knife share a same mechanical insertion port; wherein the mechanical insertion port is capable of being inserted by an integrated surgical instrument, wherein the integrated surgical instrument is provided with a trigger key;

the operation and driving unit is further configured to obtain a working mode of the inserted integrated surgical instrument, wherein the working mode of the integrated surgical instrument at least includes two modes, one mode relating to electrosurgical knife and the other mode relating to ultrasonic knife;

the operation and driving unit is further configured to control the first group of switches to be switched on, so as to deliver energy to the integrated surgical instrument through the voltage conversion unit, the first power amplification unit and the isolation conversion unit, when the trigger key is triggered; if the integrated surgical instrument currently works in the mode relating to electrosurgical knife;

the operation and driving unit is further configured to control the second group of switches to be switched on, so as to deliver energy to the integrated surgical instrument through the voltage conversion unit, the second power amplifier unit, and the isolation conversion unit, when the trigger key is triggered; if the integrated surgical instrument currently works in the mode relating to ultrasonic knife.

In an embodiment, the mode relating to electrosurgical knife includes at least three modes, the first mode relating to mono-pole electrosurgical knife, the second mode relating to neutral-pole electrosurgical knife, and the third mode relating to bi-pole electrosurgical knife;

the first group of switches include a first group of sub-switches, a second group of sub-switches, and a third group of sub-switches; the first group of sub-switches are configured to connect and disconnect an energy delivery from the isolation conversion unit to the mono-pole terminal, the second group of sub-switches are configured to connect and disconnect an energy delivery from the isolation conversion unit to the neutral-pole terminal, the third group of sub-switches are configured to connect and disconnect an energy delivery from the isolation conversion unit to the bi-pole terminal;

the operation and driving unit is further configured to control the first group of sub-switches to be switched on, so as to deliver energy to the integrated surgical instrument through the voltage conversion unit, the first power amplification unit and the isolation conversion unit, when the trigger key is triggered; if the integrated surgical instrument currently works in the mode relating to mono-pole electrosurgical knife;

the operation and driving unit is further configured to control the second group of sub-switches to be switched on, so as to deliver energy to the integrated surgical instrument through the voltage conversion unit, the first power amplification unit and the isolation conversion unit, when the trigger key is triggered; if the integrated surgical instrument currently works in the mode relating to neutral-pole electrosurgical knife;

the operation and driving unit is further configured to control the third group of sub-switches to be switched on, so as to deliver energy to the integrated surgical instrument through the voltage conversion unit, the first power amplification unit and the isolation conversion unit, when the trigger key is triggered; if the integrated surgical instrument currently works in the mode relating to bi-pole electrosurgical knife.

In an embodiment, the integrated surgical system further includes a switch component, which is configured to switch between the modes of the integrated surgical instrument.

In an embodiment, the switch component includes a foot switch.

In an embodiment, the output port for the electrosurgical knife is provided with a first group of mechanical insertion ports, and the output port for the ultrasonic knife is provided with a second group of mechanical insertion ports;

the operation and driving unit is further configured to control the first group of switches to be switched on, so as to deliver energy to the electrosurgical knife through the voltage conversion unit, the first power amplification unit and the isolation conversion unit; when a surgical instrument is inserted into the first group of mechanical insertion ports and a trigger key at said surgical instrument is triggered;

the operation and driving unit is further configured to control the second group of switches to be switched on, so as to deliver energy to the ultrasonic knife through the voltage conversion unit, the second power amplification unit and the isolation conversion unit; when a surgical instrument is inserted into the second group of mechanical insertion ports and a trigger key at said surgical instrument is triggered.

In one embodiment, the first group of mechanical insertion ports includes a mono-pole mechanical insertion port, a neutral-pole mechanical insertion port, and a bi-pole mechanical insertion port;

the first group of switches include a first group of sub-switches, a second group of sub-switches and a third group of sub-switches; the first group of sub-switches are configured to connect and disconnect an energy delivery from the isolation conversion unit to the mono-pole terminal; the second group of sub-switches are configured to connect and disconnect an energy delivery from the isolation conversion unit to the neutral-pole terminal; the third group of sub-switches are configured to connect and disconnect an energy delivery from the isolation conversion unit to the bi-pole terminal;

in order to control the first group of switches to be switched on, so as to deliver energy to the electrosurgical knife through the voltage conversion unit, the first power amplification unit and the isolation conversion unit, when a surgical instrument is inserted into the first group of mechanical insertion ports and a trigger key at the surgical instrument is triggered; the operation and driving unit is further configured to:

control the first group of sub-switches to be switched on, so as to deliver energy to the mono-pole terminal through the voltage conversion unit, the first power amplification unit and the isolation conversion unit, when a surgical instrument is inserted into the mono-pole mechanical insertion port and a trigger key at said surgical instrument is triggered;

control the second group of sub-switches to be switched on, so as to deliver energy to the neutral-pole terminal through the voltage conversion unit, the first power amplification unit and the isolation conversion unit, when a surgical instrument is inserted into the neutral-pole mechanical insertion port and a trigger key at said surgical instrument is triggered;

control the third group of sub-switches to be switched on, so as to deliver energy to the bi-pole terminal through the voltage conversion unit, the first power amplification unit and the isolation conversion unit, when a surgical instrument is inserted into the bi-pole mechanical insertion port and a trigger key at said surgical instrument is triggered.

In an embodiment, the operation and driving unit includes a wave-splitting unit, wherein the operation and driving unit is further configured to generate a third analog signal waveform, which is wave-split into at least two paths of a wave-split signal when passing through the wave-splitting unit, wherein the wave-split signal is used as the third signal;

the second power amplifier unit includes a signal conversion unit, a hardware feedback unit, and a waveform synthesis unit; a number of the signal conversion unit is same as a number of paths of the wave-split signal, each signal conversion unit is configured to receive one path of the wave-split signal, amplify said path of the wave-split wave signal and then output the amplified path of the wave-split wave signal; the waveform synthesis unit is configured to receive and synthesize an output of each signal conversion unit into one path of a sine-wave signal, and then output said sine-wave signal;

wherein when one hardware feedback unit exists, an input terminal of said hardware feedback unit is connected with an output terminal of the waveform synthesis unit, and an output terminal of said hardware feedback unit is connected with an input terminal of the wave-splitting unit; or when a number of the hardware feedback unit is same as the number of the signal conversion unit, each hardware feedback unit corresponds to one signal conversion unit, an input terminal of each hardware feedback unit is connected with an output terminal of a corresponding signal conversion unit, and an output terminal of said each hardware feedback unit is connected with an input terminal of said corresponding signal conversion unit;

wherein the hardware feedback unit is configured to feedback a signal, which is received by its input terminal, to its output terminal, so as to enable said sine-wave signal, which is outputted by the waveform synthesis unit, to be a desired sine-wave signal.

In an embodiment, when the number of the hardware feedback unit is the same as the number of the signal conversion unit, the hardware feedback unit is configured to enable a target waveform signal, which is outputted by the waveform synthesis unit, to be the desired sine-wave signal.

In an embodiment, the hardware feedback unit includes one or more of a power amplifier circuit, a resistor, a capacitor, an inductor, a diode, and a transistor.

In an embodiment, the voltage conversion unit includes a step-up circuit, which is configured to receive a negative DC voltage, and convert the negative DC voltage into a positive DC voltage according to the first control signal.

In an embodiment, the step-up circuit includes one or more step-up branches; each step-up branch includes an energy conversion inductor, a charging switch, and a discharging switch; wherein the charging switch and the discharging switch are configured to be switched on and off according to the first control signal, so as to charge and discharge the energy conversion inductor for voltage step-up.

In an embodiment, one terminal of the energy conversion inductor is grounded, the other terminal of the energy conversion inductor is connected with a voltage input terminal of the step-up circuit through the charging switch, wherein the voltage input terminal of the step-up circuit is configured to receive the negative DC voltage; the other terminal of the energy conversion inductor, which terminal is not grounded, is further connected with a voltage output terminal of the step-up circuit through the discharging switch, wherein the voltage output terminal of the step-up circuit is configured to output the positive DC voltage.

In an embodiment, the voltage conversion unit is configured to receive a negative voltage and output an adjustable positive voltage; wherein the voltage conversion unit includes one inductive element and two switch elements; one terminal of the inductive element and one terminal of each of the two switch elements are connected together, the other terminal of the inductive element is grounded, the other terminals of the two switch elements are respectively used as an input terminal and an output terminal, wherein respective switching-on times of the two switch elements are staggered, so as to realize a voltage conversion function.

In an embodiment, the voltage conversion unit includes a positive input terminal, a negative input terminal, a positive output terminal, and a negative output terminal; wherein the voltage conversion unit is configured to receive the input voltage through the positive input terminal and the negative input terminal, and output, through the positive output terminal and the negative output terminal, the DC voltage which drives the first power amplifier unit or the full-bridge power amplifier circuit and the DC voltage which is delivered to the second power amplifier unit or the linear power amplifier circuit.

In an embodiment, a range of a positive DC voltage, which voltage is outputted by the voltage conversion unit, is from 0 to a preset value of 350V.

According to the integrated surgical system of above embodiments, an electrosurgical knife function and an ultrasonic knife function are integrated in one device system.

BRIEF DESCRIPTION OF THE DRAWINGS

FIG. 11 (*a*) and FIG. 11 (*b*) are structural diagrams of an operation and driving unit according to two embodiments.

FIG. 22 (*a*), FIG. 22 (*b*), and FIG. 22 (*c*) are structural diagrams of a second power amplifier unit according to three embodiments.

DESCRIPTION OF THE PREFERRED EMBODIMENTS

This disclosure is further described in detail below through specific embodiments in combination with the accompanying drawings. In different embodiments, similar elements adopt associated similar reference numbers. In the following embodiments, many details are described in order to make this disclosure better understood. However, one skilled in the art can easily recognize that some of the features can be omitted in different cases, or can be replaced by other elements, materials and methods. In some cases, some operations related to this disclosure are not shown or described in the description, in order to avoid the core part of this disclosure being inundated by too many descriptions. For one skilled in the art, it is not necessary to describe these related operations in detail, as they can fully understand the relevant operations according to the description in this disclosure and the general technical knowledge in the art.

In addition, the features, operations, or characteristics described in the description may be combined in any appropriate manner to form various embodiments. At the same time, the steps or actions in the method description can also be exchanged or adjusted sequentially in a manner obvious to one skilled in the art. Therefore, the various sequences in the description and the drawings are only for the purpose of clearly describing a certain embodiment, and do not mean that they are necessary sequences. Unless it is otherwise specified that one of the sequences must be followed.

The terms "first", "second", etc. in the description are operable to distinguish different objects, rather than to describe a specific order. In addition, the terms "connection", and "linkage" mentioned in this disclosure include direct and indirect connection (linkage), unless otherwise specified.

In some embodiments, supplying power to the electrosurgical knife refers to supplying electric power (such as high-frequency energy) to the electrosurgical knife; supplying power to the ultrasonic knife refers to supplying electric power (such as low-frequency energy) to the ultrasonic knife.

Figure 1:
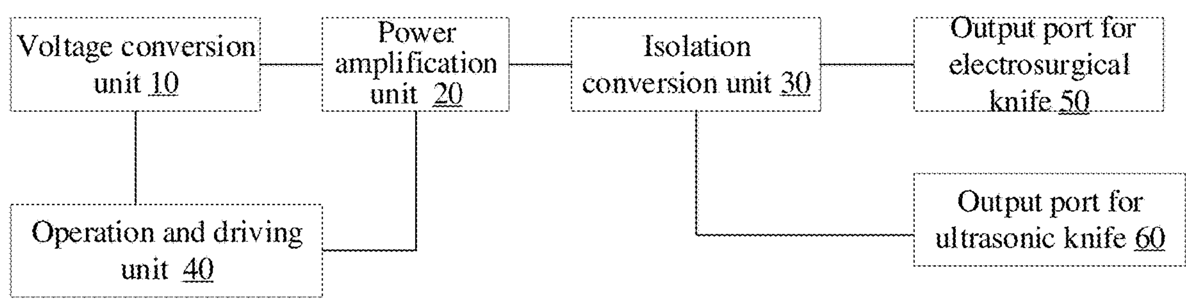
FIG. 1 is a structural diagram of an embodiment of an integrated surgical system according to an embodiment.
Figure 2A:
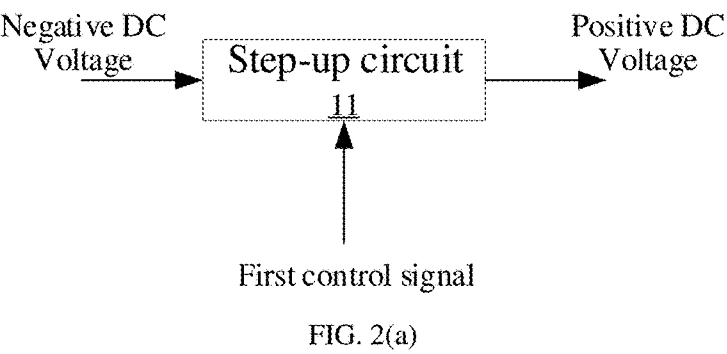
FIG. 2 (*a*), FIG. 2 (*b*), FIG. 2 (*c*), FIG. 2 (*d*), FIG. 2 (*e*), and FIG. 2 (*f*) are schematic structural diagrams of voltage conversion units of several embodiments.
Figure 2B:
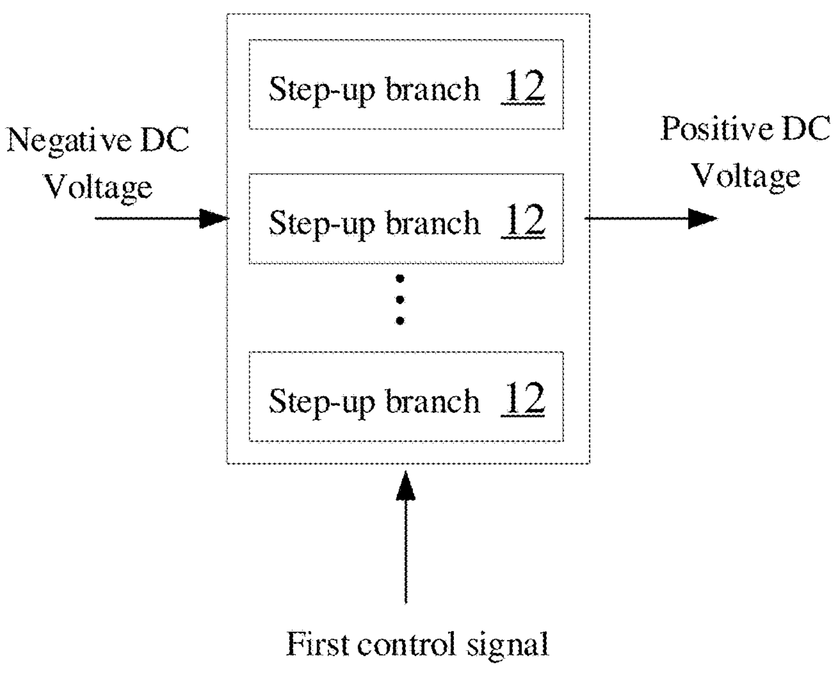
Figure 2C:
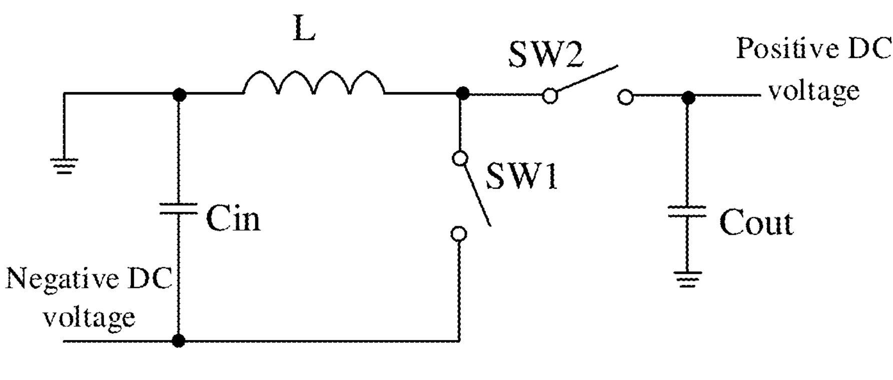
Figure 2D:
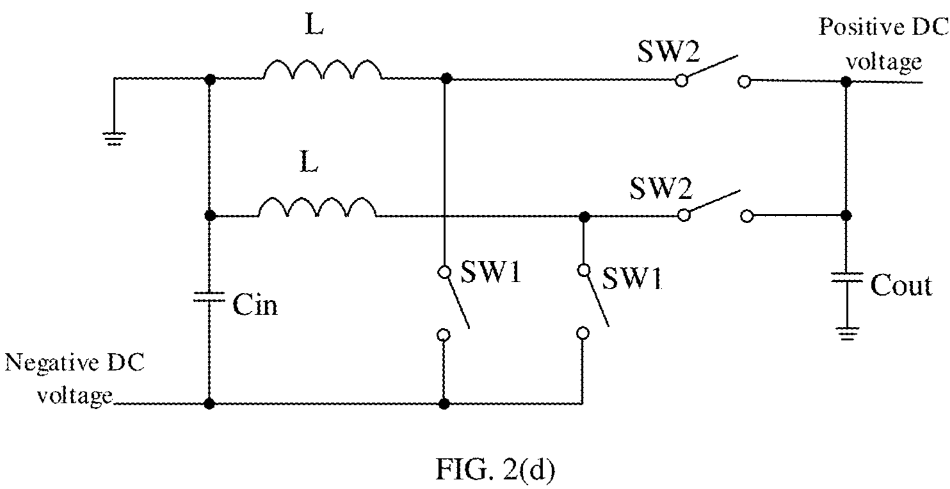
Figure 2E:
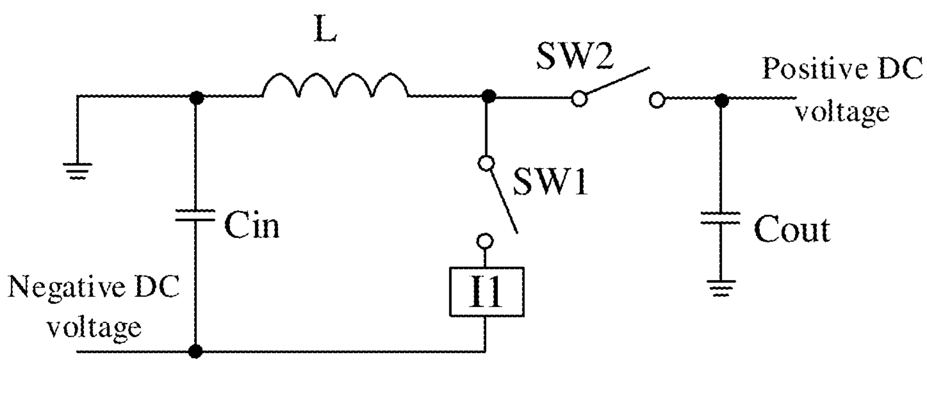
Figure 2F:
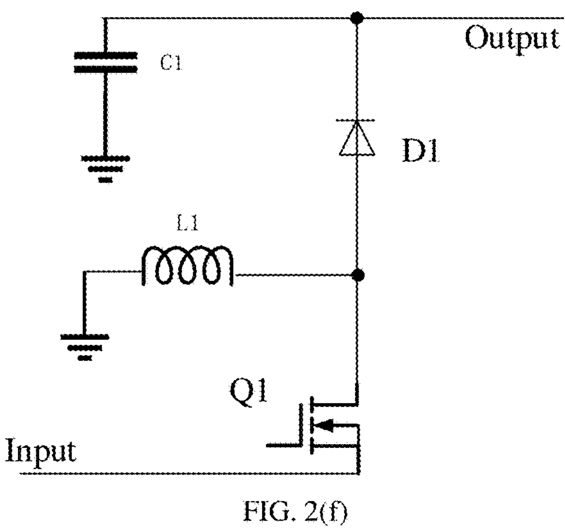

Referring to FIG. 1, an integrated surgical system in some embodiments includes a voltage conversion unit 10, a power amplification unit 20, an isolation conversion unit 30, an operation and driving unit 40, an output port for an electrosurgical knife 50 and an output port for an ultrasonic knife 60, which are described in detail below.

The voltage conversion unit 10 is configured to convert an input voltage into a DC current voltage.

In some embodiments, the voltage conversion unit 10 is a voltage conversion circuit, that is, the voltage conversion unit 10 includes a positive input terminal, a negative input terminal, a positive output terminal and a negative output terminal, and the voltage conversion unit 10 receives an input voltage through the positive input terminal and the negative input terminal, and outputs a DC voltage through the positive output terminal and the negative output terminal.

In some embodiments, the voltage conversion unit 10 can output an adjustable DC voltage. In some embodiments, the voltage conversion unit 10 outputs a DC voltage of an expected magnitude under a control of the operation and driving unit 40, for example, the voltage conversion unit 10 is configured to convert the input voltage into a DC voltage of a corresponding magnitude according to a first control signal, which is outputted by the operation and driving unit 40. In some embodiments, the first control signal is a digital signal. In some embodiments, the voltage conversion unit 10 receives a negative voltage and outputs an adjustable positive voltage. For example, the voltage conversion unit 10 receives an input voltage of-48 V, and can output a DC voltage of 0-350 V. In some embodiments, the voltage conversion unit 10 converts an AC voltage into a DC voltage. In some embodiments, the voltage conversion unit 10 is HVDC, that is, a high voltage DC unit.

Referring to FIG. 2 (*a*), in some embodiments, the voltage conversion unit 10 includes a step-up circuit 11. In some embodiments, the step-up circuit 11 is configured to receive a negative DC voltage, and convert the negative DC voltage into a positive DC voltage of a corresponding magnitude according to the first control signal. Referring to FIG. 2 (*b*), FIG. 2 (*c*) and FIG. 2 (*d*), the step-up circuit 11 of some embodiments includes one or more step-up branches 12; each step-up branch includes an energy conversion inductor L, a charging switch SW1, and a discharging switch SW2, wherein the charging switch SW1 and the discharging switch SW2 are configured to be switched on and off according to the first control signal, so as to charge and discharge the energy conversion inductor L, for voltage step-up. FIG. 2 (*c*) is an example including one step-up branch 12, and FIG. 2 (*d*) is an example including two step-up branches 12. By the multiple step-up branches 12, output power may be increased, and ripples may be reduced.

In some embodiments, one terminal of the energy conversion inductor L is grounded, the other terminal of the energy conversion inductor L is connected with a voltage input terminal of the step-up circuit 11 through the charging switch SW1, the voltage input terminal of the step-up circuit 11 is configured to receive the negative DC voltage, the other terminal of the energy conversion inductor, which is not grounded, is further connected with a voltage output terminal of the step-up circuit 11 through the discharging switch SW2, and the voltage output terminal of the step-up circuit 11 is configured to output the positive DC voltage.

During operation, the charging switch SW1 and the discharging switch SW2 are alternately turned on, and cannot be turned on at the same time, so as to adjust the output voltage by adjusting a duty ratio of the charging switch SW1 and the discharging switch SW2. Specifically, when the charging switch SW1 is turned on and the discharging switch SW2 is turned off, the energy conversion inductor L is charged through the input negative DC voltage; and when the charging switch SW1 is turned off and the discharging switch SW2 is turned on, the energy conversion inductor L is discharged through the input negative DC voltage.

In some embodiments, the charging switch SW1 includes a three-terminal transistor or a diode. In some embodiments, the discharging switch SW2 includes a three-terminal transistor or a diode.

In some embodiments, the step-up circuit 11 further includes an input capacitor Cin and/or an output capacitor Cout. One terminal of the input capacitor Cin is grounded, and the other terminal of the input capacitor Cin is connected with the voltage input terminal of the step-up circuit 11. One terminal of the output capacitor Cout is grounded, and the other terminal of the output capacitor Cout is connected with the voltage output terminal of the step-up circuit 11.

In some embodiments, referring to FIG. 2 (*e*), the step-up branch 12 further includes a current detection circuit 11, which is connected in series with the charging switch SW1 for outputting a detected current; and the operation and driving unit 40 is configured to generate or adjust the first control signal according to the detected current.

In some embodiments, the step-up circuit 11 is a Boost circuit.

In some embodiments, the positive DC voltage, which is outputted by the step-up circuit 11 ranges from 0 to a preset value. In some embodiments, the preset value is 350 V.

In some embodiments, the positive DC voltage herein includes 0.

In some embodiments, the input negative DC voltage is-48V.

A wide-range adjustable positive voltage with a minimum voltage of 0 is achieved by means of negative voltage input, so as to achieve a power adjustment of a wide dynamic range.

In an adjustable power supply system that delivers energy to a surgical device, a front end generally has an AC-to-DC function, and a wide range of adjustable positive voltages are outputted based on the DC voltage. Some solutions are that conversion is implemented on the basis of PFC (Power Factor Correction, Power Factor Correction) by using flyback. Due to the fact that the output voltage of the AC-to-DC front-end is generally not very low nor very high, the former makes the influence of a leakage inductance of the flyback scheme become large and results in low efficiency, the latter makes an adjustment range of the output voltage of the traditional Boost circuit too narrow (can only boost). In some embodiments of this disclosure, through a negative input power source, an adjustable output of a wide-range positive voltage with a minimum voltage of 0 is achieved, the efficiency is high, the defects of the above two situation are overcome, and the advantages of the above two situation are both considered.

In some embodiments of this disclosure, compared with the flyback scheme, an isolation transformer is omitted, and the efficiency is higher. Compared with a four-switch tube scheme, the output voltage can be higher, the number of switch tubes is smaller, and the cost is reduced. Compared with a traditional Boost scheme, an adjustable range of the output voltage is wider, and a voltage output of positive zero can be supported.

In some embodiments, the voltage conversion unit 10 includes an inductive element and two switch elements, one terminal of the inductive element and one terminal of each of the two switch elements are connected together, the other terminal of the inductive element is grounded, the other terminals of the two switch elements are respectively used as an input terminal and an output terminal, and respective switching-on times of the two switch elements are staggered, so as to realize a voltage conversion function. FIG. 2 (*f*) is an example of a voltage conversion unit 10, including an inductor L1, a transistor Q1, a diode D1, and a capacitor C1. One terminal of the inductor L1 is grounded, the other terminal of the inductor L1 is connected with an anode of the diode D1, a cathode of the diode D1 is connected with one terminal of the capacitor C1, and the other terminal of the capacitor C1 is grounded. The anode of the diode D1 is also connected with a first electrode of the transistor Q1. A control electrode of the transistor Q1 is controlled by the operation and driving unit 40, such as for receiving an output signal of the operation and driving unit 40, such as the first control signal mentioned above. A second electrode of the transistor Q1 is used as an input terminal of the voltage conversion unit 10 and is configured to receive an input voltage. A cathode of the diode D1 is used as an output terminal of the voltage conversion unit 10 and is configured to output an adjustable DC voltage. In the example of FIG. 2, the diode D, and the transistor Q1 are used as two switch elements, and under the control of the operation and driving unit 40, switching-on time of the diode D and switching-on time of the transistor Q1 are staggered, so as to realize a voltage conversion function.

It should be noted that the transistor mentioned herein is a three-terminal device, which may be a transistor of any structure, such as a bi-pole transistor (BJT) or a field effect transistor (FET). When the transistor is a bi-pole transistor, the control electrode of the transistor refers to a gate of the bi-pole transistor, the first electrode may be a collector or an emitter of the bi-pole transistor, the corresponding second electrode may be an emitter or a collector of the bi-pole transistor. In the actual application process, the "emitter" and "collector" may be interchanged according to the flow direction of the signal. When the transistor is a field effect transistor, the control electrode of the transistor refers to a gate electrode of the field effect transistor, the first electrode may be a drain electrode or a source electrode of the field effect transistor, a corresponding second electrode may be a source electrode or a drain electrode of the field effect transistor; wherein the "source" and "drain" may be interchanged depending on the flow direction of the signal.

In some embodiments, the power amplification unit 20 receives an output of the voltage conversion unit 10 and an output of the operation and driving unit 40, for outputting. The output of the power amplification unit 20 is provided to the output port for the electrosurgical knife 50 and the output port for the ultrasonic knife 60 after passing through the isolation conversion unit 30, so as to supply power to the electrosurgical knife and supply power to the ultrasonic knife. For example, the power amplifier unit 20 can separately supply power to the electrosurgical knife, or separately supply power to the ultrasonic knife, and can also supply power to both the electrosurgical knife and the ultrasonic knife at the same time.

In some embodiments, the power amplifier unit 20 is configured to convert the DC voltage which is outputted by the voltage conversion unit 10 into an AC voltage and amplify the AC voltage, and then provide the amplified AC voltage to the output port for the electrosurgical knife 50 after passing through the isolation conversion unit 30, so as to supply power to the electrosurgical knife. For example, under the control of the operation and driving unit 40, the power amplifier unit 20 converts the DC voltage which is outputted by the voltage conversion unit 10 into an AC voltage and amplifies the AC voltage. In some embodiments, the power amplifier unit 20 is configured to convert the DC voltage which is outputted by the voltage conversion unit 10 into an AC voltage and amplify the AC voltage according to a second control signal, which is outputted by the operation and driving unit 40. In some embodiments, the second control signal is a digital signal. In some embodiments, the power amplifier unit 20 converts the DC voltage which is outputted by the voltage conversion unit 10 into a square-wave voltage or a square-wave signal.

The above is explanation for that the power amplification unit 20 completes power supply or energy supply of the electrosurgical knife; while the explanation for that the power amplification unit 20 can also complete power supply or energy supply to the ultrasonic knife, is as below in detail.

In some embodiments, the power amplification unit 20 amplifies a third signal and then outputs the amplified third signal, wherein the power amplification unit 20 receives the power supply of the voltage conversion unit 10. In other words, the power amplification unit 20 amplifies the third signal and outputs the amplified third signal, under the power supply of the DC voltage which is outputted by the voltage conversion unit 10; and then the outputted third signal is provided to the output port for the ultrasonic knife 60 after passing through the isolation conversion unit 30, so as to supply power to the ultrasonic knife. The third signal may be generated and outputted by the operation and driving unit 40. In some embodiments, the power amplifier unit 20 outputs a periodic signal having a complete sine-wave without crossover distortion. In some embodiments, the third signal includes two paths of drive current signals, such as a current signal IA and a current signal IB, and the power amplifier unit 20 amplifies the third signal and then outputs the amplified third signal to obtain, for example, a current signal K*(IA−IB), wherein K is an amplification factor. In some embodiments, the third signal is an analog signal, for example, the third signal includes two paths of drive current signals, both of which are analog signals, for example, both the current signal IA and the current signal IB mentioned above are analog signals.

Figure 3:
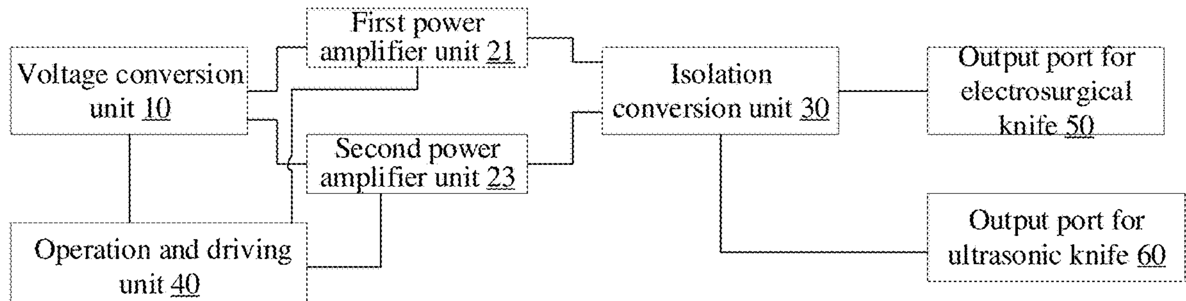
FIG. 3 is a structural diagram of an integrated surgical system according to an embodiment.

The power amplifier unit 20 has a plurality of implementations. For example, the power amplifier unit 20 can be implemented through one power amplifier circuit, or two power amplifier circuits. In some embodiments, referring to FIG. 3, the power amplifier unit 20 includes a first power amplifier unit 21 and a second power amplifier unit 23, which are described in detail below.

In some embodiments, the first power amplification unit 21 is configured to convert the DC voltage which is outputted by the voltage conversion unit 10 into an AC voltage, and amplify the AC voltage, and then provide the amplified AC voltage to the output port for the electrosurgical knife 50 after passing through the isolation conversion unit 30, so as to supply power to the electrosurgical knife. For example, under the control of the operation and driving unit 40, the first power amplification unit 21 converts the DC voltage which is outputted by the voltage conversion unit 10 into an AC voltage and amplifies the AC voltage. In some embodiments, the first power amplifier unit 21 is configured to convert the DC voltage which is outputted by the voltage conversion unit 10 into an AC voltage and amplify the AC voltage according to a second control signal, which is outputted by the operation and driving unit 40. In some embodiments, the second control signal is a digital signal. In some embodiments, the first power amplification unit 21 converts the DC voltage which is outputted by the voltage conversion unit 10 into a square-wave voltage or a square-wave signal.

Figure 4:
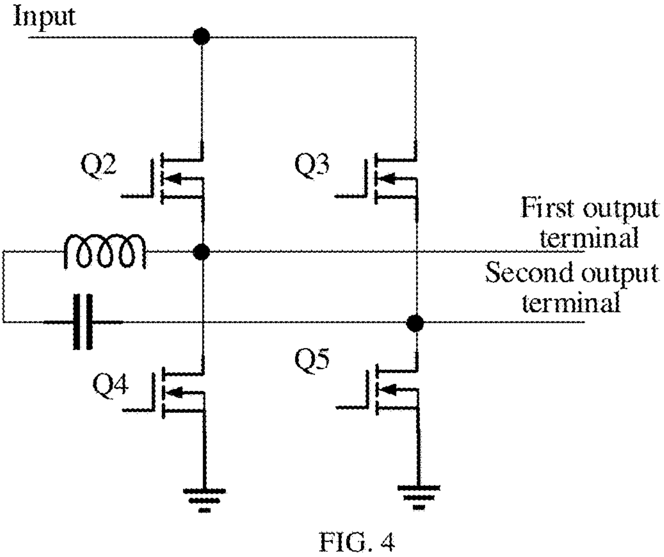
FIG. 4 is a structural diagram of a first power amplifier unit according to an embodiment.

In some embodiments, the first power amplifier unit 21 is a full-bridge power amplifier circuit. FIG. 4 is an example of a first power amplifier unit 21, which includes a transistor Q2, a transistor Q3, a transistor Q4, and a transistor Q5. A first electrode of the transistor Q2 is connected with a first electrode of the transistor Q3, and configured to receive a DC voltage which is outputted by the voltage conversion unit 10. A second electrode of the transistor Q2 is connected with a first electrode of the transistor Q4 and used as a first output terminal of the first power amplifier unit 21. A second electrode of the transistor Q3 is connected with a first electrode of the transistor Q5 and used as a second output terminal of the first power amplifier unit 21. Second electrodes of the transistor Q4 and of the transistor Q5 are both grounded. Control electrodes of the transistor Q2, transistor Q2, of the transistor Q4 and of the transistor Q5 are all controlled by the operation and driving unit 40, for example, for receiving a signal, which is outputted by the operation and driving unit 40, for example, the second control signal, wherein the second control signal may be a pulse-width modulation signal. The first power amplifier unit 21 outputs through the first output terminal and the second output terminal of the first power amplifier unit 21, for example, an AC voltage or signal, which is outputted after converting and amplifying the DC voltage which is outputted by the voltage conversion unit 10. In some embodiments, an LC series circuit is further connected between two output terminals of the full-bridge power amplifier circuit, for example, an LC series circuit is connected between the second electrode of the transistor Q2 and the second electrode of the transistor Q3, which helps the full-bridge power amplifier circuit to implement soft switching.

In some embodiments, the second power amplification unit 23 amplifies the third signal and then outputs the amplified third signal, wherein the second power amplification unit 23 receives the power supply of the voltage conversion unit 10. In other words, the second power amplification unit 23 amplifies the third signal and outputs the amplified third signal, under the power supply of the DC voltage which is outputted by the voltage conversion unit 10; and then the outputted third signal is provided to the output port for the ultrasonic knife 60 after passing through the isolation conversion unit 30, so as to supply power to the ultrasonic knife 60. The third signal may be generated and outputted by the operation and driving unit 40. In some embodiments, the second power amplifier unit 23 outputs a periodic signal having a complete sine-wave without crossover distortion. In some embodiments, the third signal includes two paths of drive current signals, such as a current signal IA and a current signal IB, and the second power amplifier unit 23 amplifies the third signal and then outputs the amplified third signal to obtain, for example, a current signal K*(IA−IB), wherein K is an amplification factor. In some embodiments, the third signal is an analog signal, for example, the third signal includes two paths of drive current signals, both of which are analog signals, for example, both the current signal IA and the current signal IB mentioned above are analog signals.

In some embodiments, the second power amplifier unit 23 is a linear power amplifier circuit.

Figure 5:
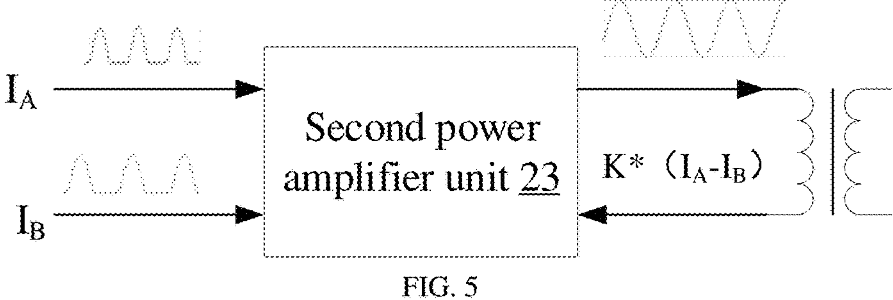
FIG. 5 is a working principal diagram of a second power amplifier unit according to an embodiment.

Referring to FIG. 5, the second power amplifier unit 23 is driven by two paths of drive signals, such as a current signal IA and a current signal IB, so as to output K*(IA−IB) to ensure that IA−IB is a complete sine-wave without crossover distortion and waveform distortion, such that a relatively ideal result can be achieved by means of a hardware circuit in a low cost, which is further described below.

It can be seen that, in an embodiment in which the power amplifier unit 20 includes the first power amplifier unit 21 and the second power amplifier unit 23, the voltage conversion unit 10 is configured to convert the input voltage, according to the first control signal, into a DC voltage which drives the first power amplifier unit 21, or into a DC voltage which is delivered to the second power amplifier unit 23, that is, converting the input voltage into a working voltage of the second power amplifier unit 23, wherein the working voltage is a DC voltage.

Figure 6:
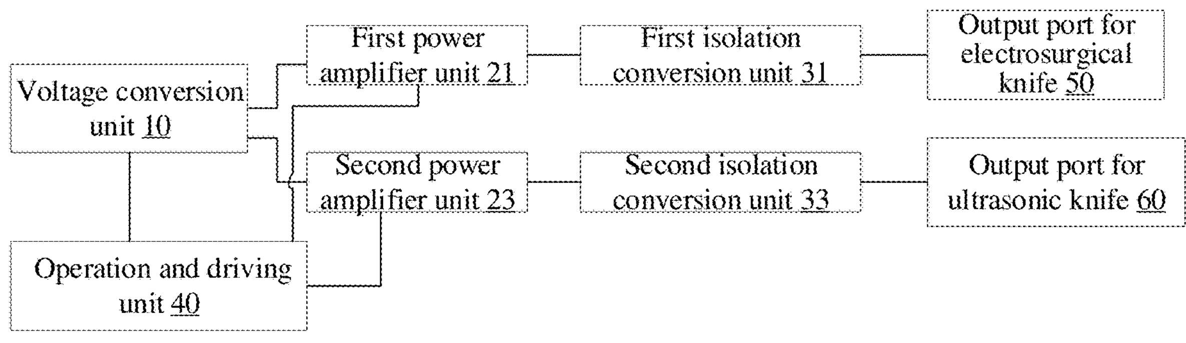
FIG. 6 is a structural diagram of an integrated surgical system according to an embodiment.

In some embodiments, referring to FIG. 6, the isolation conversion unit 30 includes a first isolation conversion unit 31 and a second isolation conversion unit 33, which are described in detail below.

In some embodiments, the first isolation conversion unit 31 is configured to perform isolation and conversion on the AC voltage which is outputted by the power amplification unit 20, and then provide the amplified AC voltage to the output port for the electrosurgical knife 50. In some embodiments, the first isolation conversion unit 31 is configured to perform resonance, isolation and conversion on the AC voltage which is outputted by the power amplification unit 20, and then provide the amplified AC voltage to the output port for the electrosurgical knife 50.

In an embodiment, in which the power amplification unit 20 includes the first power amplification unit 21, the first isolation conversion unit 31 is configured to perform isolation and conversion on the AC voltage which is outputted by the first power amplification unit 21 and then provide the amplified AC voltage to the output port for the electrosurgical knife 50. In some embodiments, the first isolation conversion unit 31 is configured to perform resonance, isolation and conversion on the AC voltage which is outputted by the first power amplification unit 21 and then provide the amplified AC voltage to the output port for the electrosurgical knife 50.

In an example that the first power amplifier unit 21 is implemented through a full-bridge power amplifier circuit, the full-bridge power amplifier circuit is configured to convert the DC voltage which is outputted by the voltage conversion unit 10 into a square-wave voltage; and the first isolation conversion unit 31 is configured to filter the square-wave voltage into a sine-wave voltage, perform resonance, isolation and conversion on the sine-wave voltage, and then provide the sine-wave voltage to an output port for the electrosurgical knife, so as to supply power to the electrosurgical knife.

In some embodiments, the first isolation conversion unit 31 is implemented by a transformer.

The above are some descriptions of the first isolation conversion unit 31, and the following describes the second isolation conversion unit 33.

In some embodiments, the second isolation conversion unit 33 is configured to perform isolation and conversion on the amplified third signal, which is outputted by the power amplifier unit 20 after amplifying the third signal, and then provide the amplified signal to the output port for the ultrasonic knife 60.

In an embodiment in which the power amplification unit 20 includes the second power amplification unit 23, the second isolation conversion unit 33 is configured to perform isolation and conversion on the amplified third signal, which is outputted by the power amplifier unit 20 after amplifying the third signal, and then provide the amplified signal to the output port for the ultrasonic knife 60.

In some embodiments, the second isolation conversion unit 33 is implemented by a transformer.

Figure 7:
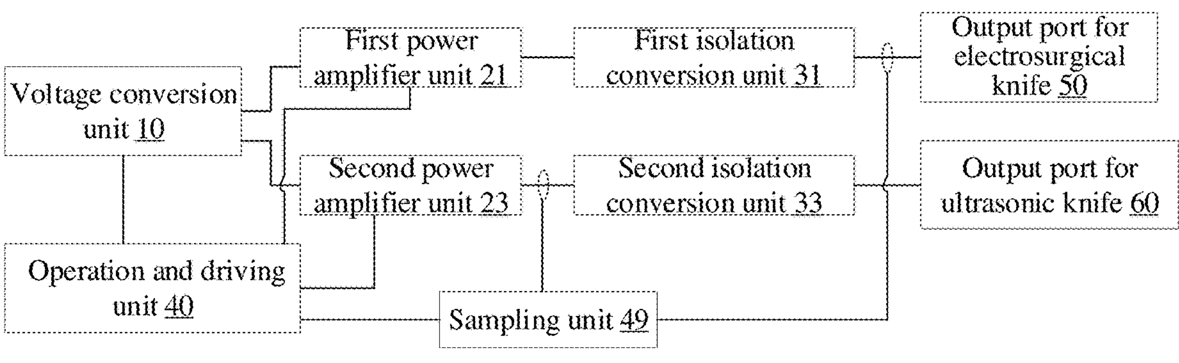
FIG. 7 is a structural diagram of an integrated surgical system according to an embodiment.

Referring to FIG. 7, the integrated surgical system of some embodiments further includes a sampling unit 49, which is described in detail below.

In some embodiments, the sampling unit 49 is configured to sample an input or an output of the isolation conversion unit 30, so as to obtain a sampled electrical signal. In some embodiments, the sampled electrical signal includes at least one of a voltage, a current, and power. The operation and driving unit 40 adjusts at least one of the first control signal, the second control signal, and the third signal, according to the sampled electrical signal.

In some embodiments, the sampled electrical signal includes a first sampled electrical signal and/or a second sampled electrical signal.

In some embodiments, the sampling unit 49 is configured to sample an input or an output of the first isolation conversion unit 31, so as to obtain a first sampled electrical signal; and the sampling unit 49 is further configured to sample an input or an output of the first isolation conversion unit 31, so as to obtain a second sampled electrical signal. In some embodiments, the first sampled electrical signal includes at least one of a voltage, a current, and power. In some embodiments, the second sampled electrical signal includes at least one of a voltage, a current, and power. In some embodiments, the operation and driving unit 40 adjusts the first control signal and/or the second control signal according to the first sampled electrical signal. In some embodiments, the operation and driving unit 40 adjusts the third signal according to the second sampled electrical signal.

Figure 8:
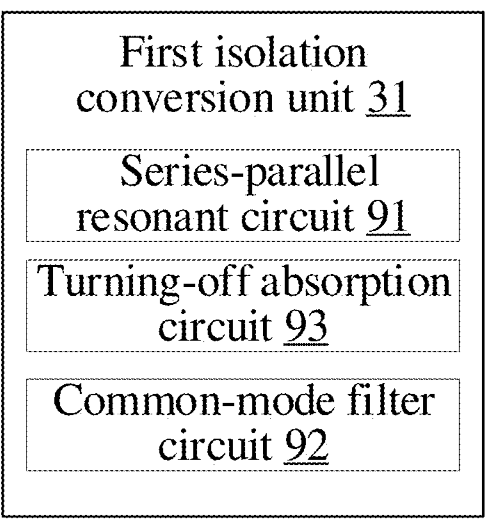
FIG. 8 is a structural diagram of a first isolation conversion unit according to an embodiment.

Referring to FIG. 8, the first isolation conversion unit 31 of some embodiments further includes at least one of a series-parallel resonant circuit 91, a common-mode filter circuit 92, and a turning-off absorption circuit 93, which is described in detail below.

In some embodiments, the series-parallel resonant circuit 91 is configured to filter the AC voltage which is outputted by the first power amplifier unit 21, for example, filter the square-wave into a sine-wave and then output the sine-wave. In an embodiment in which the power amplifier unit 20 includes the first power amplifier unit 21, the common-mode filter circuit 92 is configured to filter a common-mode signal out of an AC voltage, which voltage is outputted by the first power amplifier unit 21. In an embodiment in which the power amplification unit 20 includes the first power amplification unit 21, the turning-off absorption circuit 93 is configured to absorb oscillation after the first power amplification unit 21 is turned off.

Figure 9:
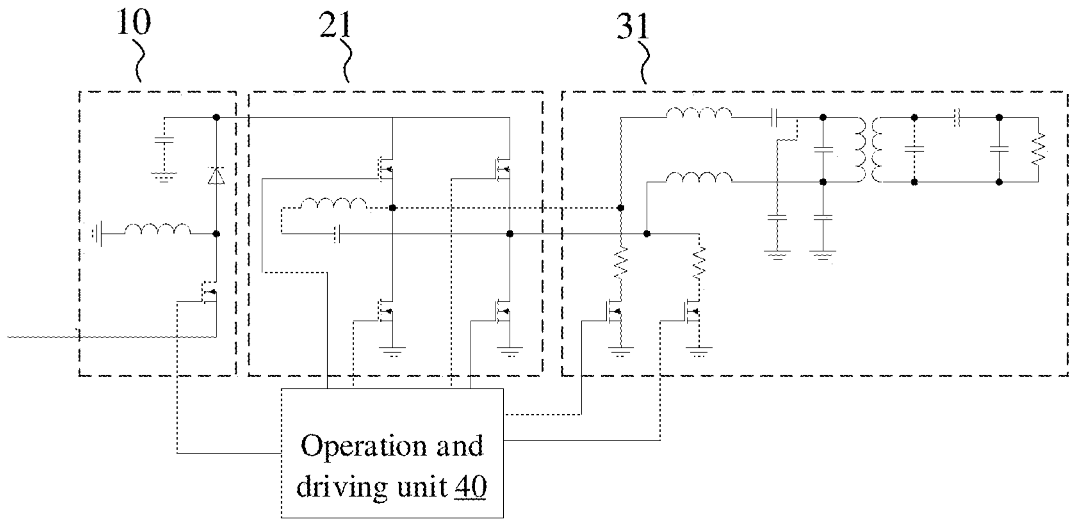
FIG. 9 is a partial structural diagram of an integrated surgical system according to an embodiment.

Referring to FIG. 9, it is an example showing a circuit diagram of a voltage conversion unit 10, a first power amplification unit 21 and a first isolation conversion unit 31, wherein the circuit diagram of the first isolation conversion unit 31 includes circuit implementation structures of a series-parallel resonant circuit 91, a common-mode filter circuit 92, a turning-off absorption circuit 93, and a first isolation conversion unit 31.

Figure 10:
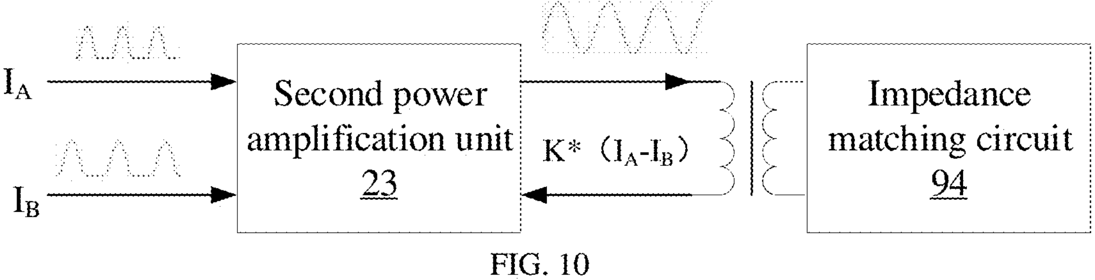
FIG. 10 is a partial structural diagram of an integrated surgical system according to an embodiment.

Referring to FIG. 10, the integrated surgical system of some embodiments further includes an impedance matching circuit 94, which is described in detail below.

In some embodiments, the impedance matching circuit 94 is connected between the power amplifier unit 20 and the isolation conversion unit 30 for impedance matching.

In an embodiment in which the power amplification unit 20 includes the second power amplification unit 23, the impedance matching circuit 94 is connected between the second power amplification unit 23 and the isolation conversion unit 30 for impedance matching.

In an embodiment in which the isolation conversion unit 30 includes the second isolation conversion unit 33, the impedance matching circuit 94 is connected between the power amplification unit 20 and the second isolation conversion unit 33 for impedance matching.

In an embodiment in which the power amplification unit 20 includes the second power amplification unit 23 and the isolation conversion unit 30 includes the second isolation conversion unit 33, the impedance matching circuit 94 is connected between the second power amplification unit 23 and the second isolation conversion unit 33 for impedance matching.

In some embodiments, the operation and driving unit 40 is configured to generate and/or adjust anyone, any two, or all three of the first control signal, the second control signal, and the third signal, which are described in detail below.

In some embodiments, the operation and driving unit 40 receives a control parameter input by the user through the user input unit.

In some embodiments, the operation and driving unit 40 is configured to generate a first control signal, a second control signal and a third signal, according to the control parameter.

In some embodiments, the operation and driving unit 40 is configured to adjust anyone, any two, or all three of the first control signal, the second control signal, and the third signal according to a sampled electrical signal.

In some embodiments, the operation and driving unit 40 is configured to adjust the first control signal and/or the second control signal according to the first sampled electrical signal, and adjust the third signal according to the second sampled electrical signal.

Referring to FIG. 11 (*a*), in some embodiments, the operation and driving unit 40 includes a processor 41, a waveform generator 43, a digital-to-analog conversion unit 45, and a wave-splitting unit 47, which are described in detail below.

In some embodiments, the processor 41 is configured to generate a first control signal. In some embodiments, referring to FIG. 11 (*b*), the operation and driving unit 40 further includes a digital-to-analog conversion unit 46, which is configured to convert the first control signal from a digital signal into an analog signal, and then output the analog signal to the voltage conversion unit 10.

In some embodiments, the processor 41 controls the waveform generator 43 to generate a second digital signal waveform as a second control signal.

In some embodiments, the processor controls the waveform generator 43 to generate a third digital signal waveform, and the digital-to-analog conversion unit 45 converts the third digital signal waveform into a third analog signal waveform as a third initial signal; and the wave-splitting unit 47 is configured to wave-split the third analog signal waveform or the third initial signal to obtain a third signal. In some embodiments, the wave-splitting unit 47 wave-splits the third analog signal waveform into at least two path of wave-split signals as the third signal.

In some embodiments, the processor 41 receives an input parameter, such as a control parameter of the user input unit, calculates parameter(s), such as amplitude, frequency, and duty cycle of a drive waveform, and sends waveform data or waveform parameters to the waveform generator 43, so as to generate the required drive waveform. The analog signal waveform is used by the second power amplifier unit 23, for example the linear power amplifier, and the digital signal waveform is used to drive the first power amplifier unit 21, for example, a full-bridge power amplifier; and the processor 41 calculates relevant electrical parameters, such as impedance, power and a phase difference according to the sampled electrical signal fed back by the sampling unit 49, and adjusts the output voltage of an output waveform and the output voltage of the voltage conversion unit 10 in real time, thereby achieving the required energy output.

Figures 11A, 11B, 12:
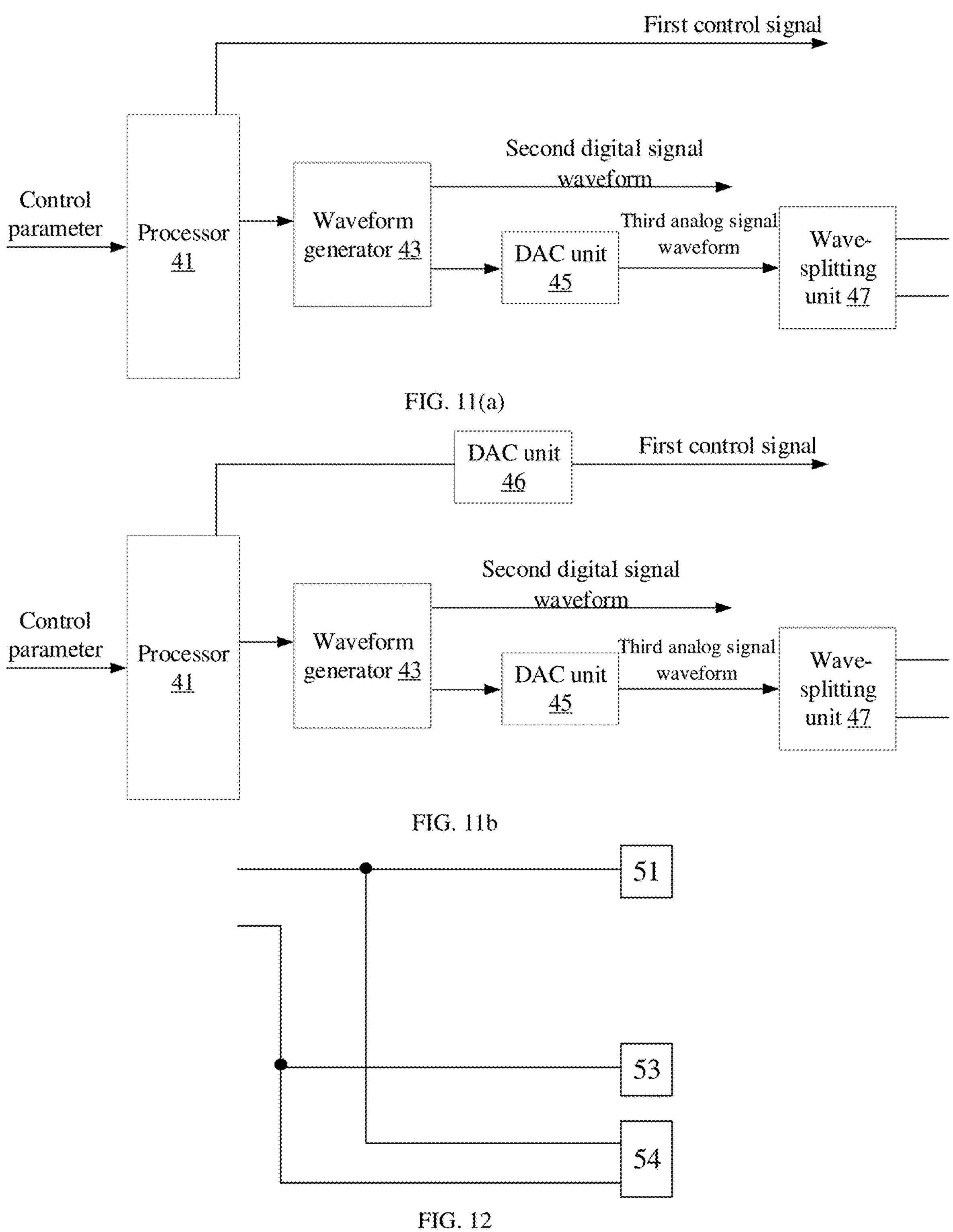
FIG. 12 is a structural diagram of an output port for an electrosurgical knife according to an embodiment.

In some embodiments, referring to FIG. 12, the output port for the electrosurgical knife 50 includes a mono-pole terminal 51, a neutral-pole terminal 53, and a bi-pole terminal 54.

Figure 13:
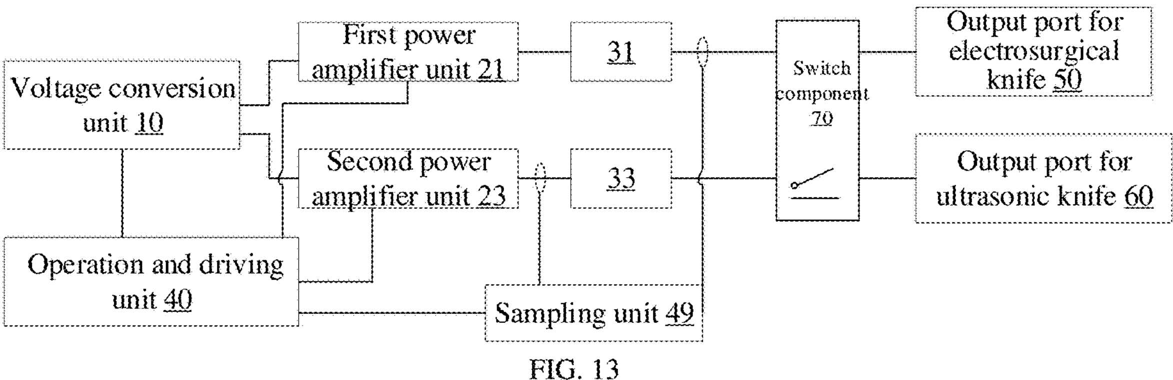
FIG. 13 is a structural diagram of an integrated surgical system according to an embodiment.

Referring to FIG. 13, the integrated surgical system of some embodiments further includes a switch component 70 for connecting and disconnecting a power supply to the output port for the electrosurgical knife 50 and the output port for the ultrasonic knife 60. In some embodiments, the switch component 70 is a manual switch component for the user to manually connect and disconnect the power supply of the output port for the electrosurgical knife 50 and the output port for the ultrasonic knife 60. For example, by means of the manual switch component 70, the user can switch on the output port for the electrosurgical knife 50, so as to supply power to the electrosurgical knife; by means of the manual switch component 70, the user can switch off the output port for the electrosurgical knife 50, so that the electrosurgical knife cannot obtain power from the output port for the electrosurgical knife 50. By means of the manual switch component 70, the user can switch on the output port for the ultrasonic knife 60, so as to supply power to the ultrasonic knife; by means of the manual switch component 70, the user can switch off the output port for the ultrasonic knife 60, so that the ultrasonic knife cannot obtain power from the output port for the ultrasonic knife 60.

In some embodiments, the electrosurgical knife may be fixedly connected with the output port for the electrosurgical knife 50 through a cable.

In some embodiments, the electrosurgical knife is connected with the output port for the electrosurgical knife 50 in a pluggable manner.

In some embodiments, the ultrasonic knife may be fixedly connected with the output port for the ultrasonic knife 60 through a cable.

In some embodiments, the ultrasonic knife is connected with the output port for the ultrasonic knife 60 in a pluggable manner.

In some embodiments, the output port for the electrosurgical knife 50 and the output port for the ultrasonic knife 60 may be the same port, and both the electrosurgical knife and the ultrasonic knife are in pluggable connection with the port.

In some embodiments, the output port for the electrosurgical knife 50 and the output port for the ultrasonic knife 60 can be the same port, the integrated surgical system can provide both electrosurgical knife energy and ultrasonic knife energy, but only one energy can be outputted at the same moment, and the energy output is determined in a pre-emptive manner. In some embodiments, the energy conversion can be completed by the operation and driving unit 40 through controlling the switch component 70.

Figure 14:
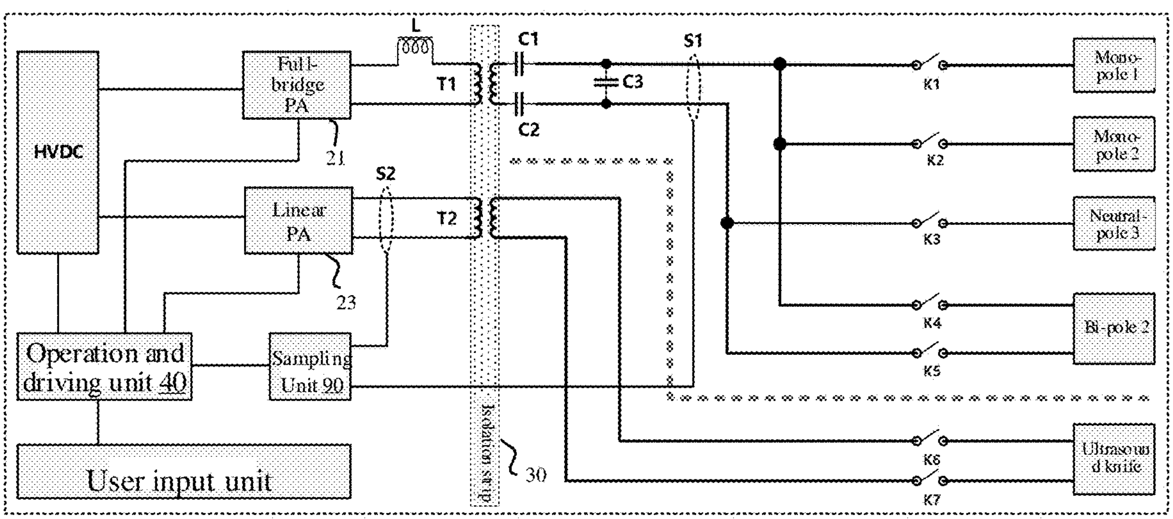
FIG. 14 is a structural diagram of an integrated surgical system according to an embodiment.

Please refer to FIG. 14, which is an example of an integrated surgical system. The integrated surgical system shown in FIG. 14 supports one path of an energy output for the ultrasonic knife, two paths of energy outputs for a mono-pole electrosurgical knife, and one path of an energy output for a bi-pole electrosurgical knife. As shown in figure(s), a power output portion of the integrated surgical system consists of two portions, including a high-frequency power generation circuit for the electrosurgical knife, which is mainly composed of a first power amplifier unit 21, such as a full-bridge power amplifier circuit (full-bridge power amplifier), and a first isolation conversion unit 31, such as a transformer T1 and associated peripheral devices; and a power driving circuit for ultrasonic knife, which is mainly composed of a second power amplifier unit 23, such as a linear power amplifier circuit (a linear power amplifier), and a first isolation conversion unit 31, such as a transformer T2. The voltage conversion unit 10, such as a high voltage DC (HVDC) power supply unit, serves as an energy source to supply power to the full-bridge power amplifier and the linear power amplifier at the same time, and the sampling unit 49, for example, the sensor S1 and the sensor S2, are respectively configured to obtain signals, such as voltage, current and power of the power generation circuit for the electrosurgical knife and the power driving circuit for the ultrasonic knife. The sensor signals are analysed by the operation and driving unit 40, and used to implement driving control over the foregoing two power amplifiers and HVDC.

In addition, the user input unit provides an operation interface, through which the user can control the outputted control parameter, such as a working mode and a power magnitude. It can be seen from the foregoing structure that the integrated surgical system samples and outputs an energy signal through the sampling unit 49, and the operation and driving unit 40 performs a feedback adjustment on the two power amplifier circuits, so as to realize a stable output at preset energy of the user input unit.

In the example of FIG. 14, the output port for the electrosurgical knife 50 includes a mono-pole terminal 1, a mono-pole terminal 2, a neutral-pole terminal and a bi-pole terminal in the figure, which can support both the two paths of energy outputs for the mono-pole electrosurgical knife and one path of an energy output for bi-pole electrosurgical knife.

In the example of FIGS. 14, K1 to K7 are selection switches for energy output of instrument channels, which are selectively connect to the corresponding instrument the output energy for the ultrasonic knife and the output energy for the electrosurgical knife, according to an instrument interface and a triggered control input signal which are selected by the user. Generally, the energy output for the electrosurgical knife and the energy output for the ultrasonic knife are in a time-division mode. That is, when the power generation circuit for the electrosurgical knife and a certain switch of the instrument channel for the electrosurgical knife (K1, K2, K3 or K4 and K5) are switched on (closed) to output energy, the power generation circuit for the ultrasonic knife does not work and switch(es) of the instrument channel for the ultrasonic knife are switched off, and there is no output energy for the ultrasonic knife. Similarly, when the energy output of the ultrasonic knife is realized, the energy output for the electrosurgical knife is switched off. In addition, since the power generation circuit for the electrosurgical knife and the power generation circuit for the ultrasonic knife are two independent circuits in this disclosure, it is also possible to support simultaneous outputs of at least two different energy instruments, that is, to output energy for the electrosurgical knife and to output energy for the ultrasonic knife at the same time.

Figure 15A:
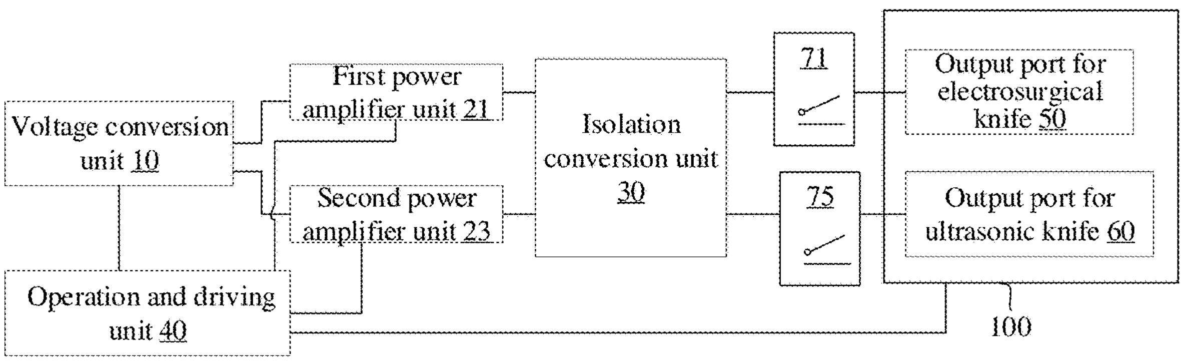
FIG. 15 (*a*) and FIG. 15 (*b*) are structural diagrams of an integrated surgical system according to two embodiments.
Figure 15B:
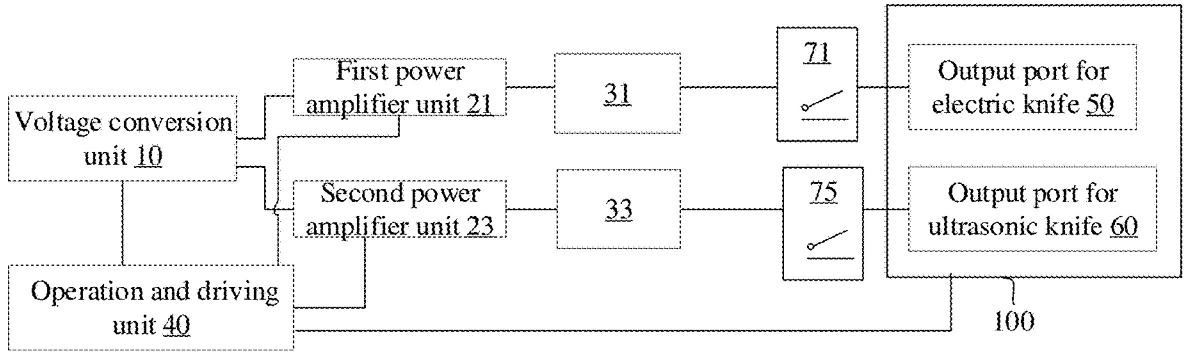

In some embodiments, referring to FIG. 15 (*a*) or FIG. 15 (*b*), the switch component 70 includes a first group of switches 71 and a second group of switches 75, wherein the first group of switches 71 are configured to connect and disconnect an energy delivery from the isolation conversion unit 30, for example, the first isolation conversion unit 31, to the output port for the electrosurgical knife 50, and the second group of switches 75 are configured to connect and disconnect an energy delivery from the isolation conversion unit 30, such as the second isolation conversion unit 33, to the output port for the ultrasonic knife 60.

In some embodiments, the output port for the electrosurgical knife 50 and the output port for the ultrasonic knife 60 share a same mechanical insertion port 100, and if a surgical instrument is inserted into the mechanical insertion port 100, energy is delivered through the voltage conversion unit 10, the first power amplification unit 21 and the isolation conversion unit 30, for example, the first isolation conversion unit 31, or energy is delivered through the voltage conversion unit 10, the second power amplification unit 23 and the isolation conversion unit 30, for example, the second isolation conversion unit 33.

In some embodiments, when the surgical instrument is inserted into the mechanical insertion port 100, the operation and driving unit 40 identifies a type of the inserted surgical instrument through the mechanical insertion port 100;

wherein the surgical instrument at least includes two types, one type is ultrasonic knife, and the other type is electrosurgical knife; wherein the surgical instrument is provided with a trigger key.

In some embodiments, situations are as follows.

The operation and driving unit 40 is configured to control the first group of switches 71 to be switched on, so as to deliver energy to the electrosurgical knife through the voltage conversion unit 10, the first power amplification unit 21 and the isolation conversion unit 30, such as a first isolation conversion unit 31, when the trigger key is triggered; if the type of the surgical instrument is currently identified as electrosurgical knife.

The operation and driving unit 40 is further configured to control the second group of switches 72 to be switched on, so as to deliver energy to the ultrasonic knife through the voltage conversion unit 10, the second power amplification unit 23 and the isolation conversion unit 30, such as a second isolation conversion unit 33, when the trigger key is triggered; if the type of the surgical instrument is currently identified as ultrasonic knife.

Figure 16:
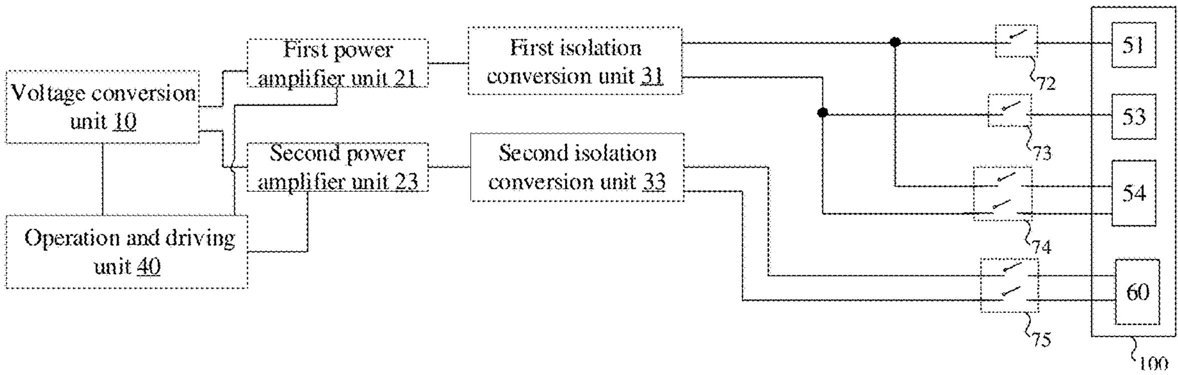
FIG. 16 is a structural diagram of an integrated surgical system according to an embodiment.

In some embodiments, referring to FIG. 16, the type of the electrosurgical knife further includes at least three types, the first type is mono-pole electrosurgical knife, the second type is neutral-pole electrosurgical knife, and the third type is bi-pole electrosurgical knife; and the output port for the electrosurgical knife 50 includes a mono-pole terminal 51, a neutral-pole terminal 53 and a bi-pole terminal 54; the first group of switches 71 includes a first group of sub-switches 72, a second group of sub-switches 73 and a third group of sub-switches 74. The first group of sub-switches 72 are configured to connect and disconnect an energy delivery from the isolation conversion unit 30 to the mono-pole terminal 51, the second group of sub-switches 73 are configured to connect and disconnect an energy delivery of the isolation conversion unit 30 to the neutral-pole terminal 53, and the third group of sub-switches 74 are configured to connect and disconnect an energy delivery of the isolation conversion unit 30 to the bi-pole terminal 54.

If the type of the surgical instrument is currently identified as mono-pole electrosurgical knife, when the trigger key is triggered, the operation and driving unit 40 controls the first group of sub-switches 72 to be switched on, so as to deliver energy to the mono-pole electrosurgical knife through the voltage conversion unit 10, the first power amplification unit 21 and the isolation conversion unit 30, for example, the first isolation conversion unit 31.

If the type of the surgical instrument is currently identified as neutral-pole electrosurgical knife, when the trigger key is triggered, the operation and driving unit 40 controls the second group of sub-switches 73 to be switched on, so as to deliver energy to the neutral-pole electrosurgical knife through the voltage conversion unit 10, the first power amplification unit 21 and the isolation conversion unit 30, for example, the first isolation conversion unit 31.

If the type of the surgical instrument is currently identified as bi-pole electrosurgical knife, when the trigger key is triggered, the operation and driving unit controls the third group of sub-switches 74 to be switched on, so as to deliver energy to the bi-pole electrosurgical knife through the voltage conversion unit 10, the first power amplification unit 21 and the isolation conversion unit 30, such as the first isolation conversion unit 31.

The identification of the type of the surgical instrument may be determined by an identification code stored in a memory inside the surgical instrument, and when the surgical instrument is inserted into the mechanical insertion port 100, the operation and driving unit 40 is connected with the surgical instrument through a communication line, so that the operation and driving unit 40 may identify the type of the surgical instrument.

In some embodiments, the mechanical insertion port 100 may also be configured to be inserted by an integrated surgical instrument, and the working mode of the integrated surgical instrument includes at least two modes, one mode relating to electrosurgical knife and the other mode relating to ultrasonic knife.

In some embodiments, the mechanical insertion port 100 is capable of being inserted by an integrated surgical instrument, that is, the surgical instrument may be an integrated surgical instrument, and the integrated surgical instrument is provided with a trigger key.

The operation and driving unit 40 obtains a working mode of the inserted integrated surgical instrument, and the working mode of the integrated surgical instrument at least includes two modes, one mode relating to electrosurgical knife and the other mode relating to ultrasonic knife.

If the integrated surgical instrument currently works in the mode relating to electrosurgical knife, when the trigger key is triggered, the operation and driving unit 40 controls the first group of switches 71 to be switched on, so as to deliver energy to the integrated surgical instrument through the voltage conversion unit 10, the first power amplification unit 21 and the isolation conversion unit 30, for example, the first isolation conversion unit 31.

If the integrated surgical instrument currently works in the mode relating to ultrasonic knife, when the trigger key is triggered, the operation and driving unit 40 controls the second group of switches 75 to be switched on, so as to deliver energy to the integrated surgical instrument through the voltage conversion unit 10, the second power amplification unit 23 and the isolation conversion unit 30, such as the second isolation conversion unit 33.

In some embodiments, the mode relating to electrosurgical knife of the integrated surgical instrument further includes at least three modes, the first mode relating to mono-pole electrosurgical knife, the second mode relating to neutral-pole electrosurgical knife, and the third mode relating to bi-pole electrosurgical knife;

the output port for the electrosurgical knife 50 includes a mono-pole terminal 51, a neutral-pole terminal 53, and a bi-pole terminal 54; the first group of switches 71 includes a first group of sub-switches 72, a second group of sub-switches 73 and a third group of sub-switches 74; the first group of sub-switches 72 are configured to connect and disconnect an energy delivery from the isolation conversion unit 30 to the mono-pole terminal 51; the second group of sub-switches 73 are configured to connect and disconnect an energy delivery from the isolation conversion unit 30 to the neutral-pole terminal 53; the third group of sub-switches 74 are configured to connect and disconnect an energy delivery from the isolation conversion unit 30 to the bi-pole terminal 54.

If the integrated surgical instrument currently works in the mode relating to mono-pole electrosurgical knife; when the trigger key is triggered, the operation and driving unit 40 controls the first group of sub-switches 72 to be switched on, so as to deliver energy to the integrated surgical instrument through the voltage conversion unit 10, the first power amplification unit 21 and the isolation conversion unit 30, for example, the first isolation conversion unit 31.

If the integrated surgical instrument currently works in the mode relating to neutral-pole electrosurgical knife; when the trigger key is triggered, the operation and driving unit 40 controls the second group of sub-switches 73 to be switched on, so as to deliver energy to the integrated surgical instrument through the voltage conversion unit 10, the first power amplification unit 21 and the isolation conversion unit 30, for example, the first isolation conversion unit 31.

If the integrated surgical instrument currently works in the mode relating to bi-pole electrosurgical knife, the operation and driving unit 40 controls the third group of sub-switches 74 to be switched on, so as to deliver energy to the integrated surgical instrument through the voltage conversion unit 10, the first power amplification unit 21 and the isolation conversion unit 30, such as the first isolation conversion unit 31.

Figure 17:
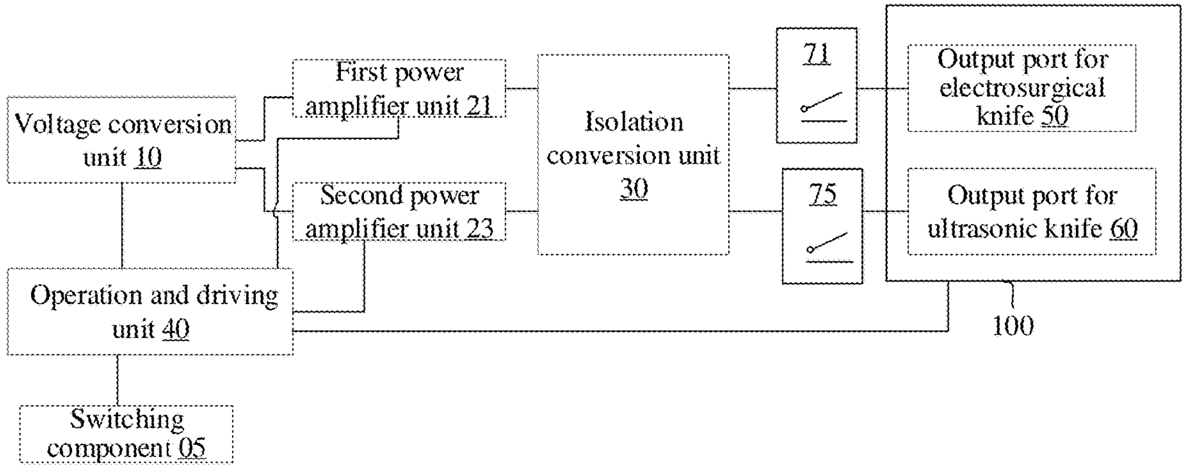
FIG. 17 is a structural diagram of an integrated surgical system according to an embodiment.

In some embodiments, referring to FIG. 17, the integrated surgical system includes a switch component 05, and the switch component 05 is configured to switch the modes of the integrated surgical instrument. For example, the switch component 05 switches the integrated surgical instrument from the mode relating to electrosurgical knife to the mode relating to ultrasonic knife, or switches the integrated surgical instrument from the mode relating to ultrasonic knife to the mode relating to electrosurgical knife. In some embodiments, the switch component 05 includes a foot switch. In some embodiments, the switch component 05 may include two foot switches, one foot switch is configured to switch the integrated surgical instrument from the mode relating to electrosurgical knife to the mode relating to ultrasonic knife, or switch the integrated surgical instrument from the mode relating to ultrasonic knife to the mode relating to electrosurgical knife, and the other foot switch is configured to switch the integrated surgical instrument between the mode relating to mono-pole electrosurgical knife, the mode relating to neutral-pole electrosurgical knife, and the mode relating to bi-pole electrosurgical knife.

Figure 18:
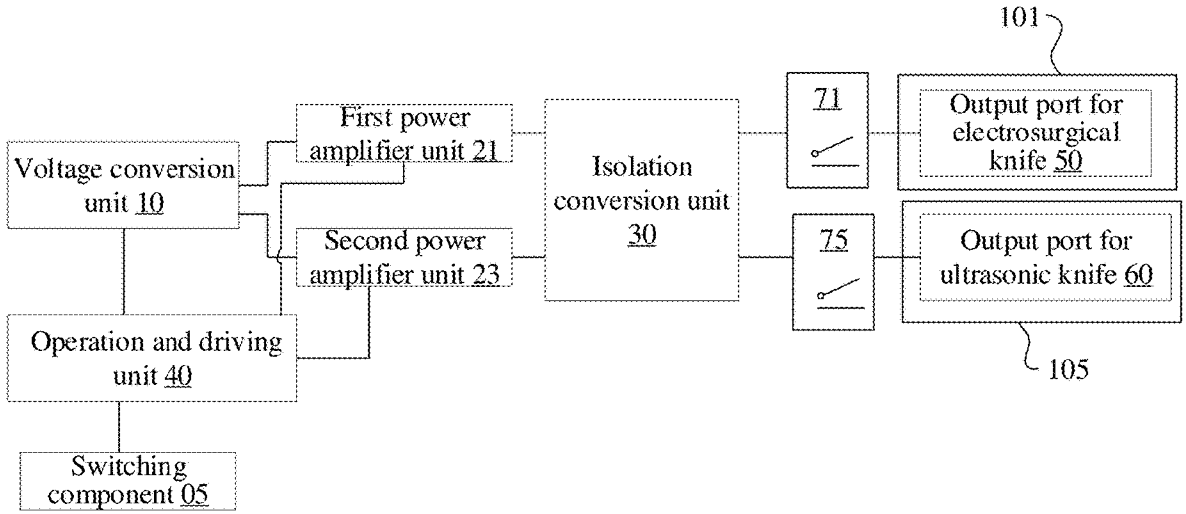
FIG. 18 is a structural diagram of an integrated surgical system according to an embodiment.

In some embodiments, referring to FIG. 18, the output port for the electrosurgical knife 50 is provided with a first group of mechanical insertion ports 101, and the output port for the ultrasonic knife 60 is provided with a second group of mechanical insertion ports 105. In some embodiments, when the surgical instrument is inserted into the first group of mechanical insertion ports 101, and the trigger key at the surgical instrument is triggered, the operation and driving unit 40 controls the first group of switches 71 to be switched on, so as to deliver energy to the electrosurgical knife through the voltage conversion unit 10, the first power amplification unit 21 and the isolation conversion unit 30, such as the first isolation conversion unit 31. When the surgical instrument is inserted into the second group of mechanical insertion ports 105, the operation and driving unit 40 controls the second group of switches 75 to be switched on, so as to deliver energy to the ultrasonic knife through the voltage conversion unit 10, the second power amplification unit 23 and the isolation conversion unit 30, for example, the second isolation conversion unit 33.

Figure 19:
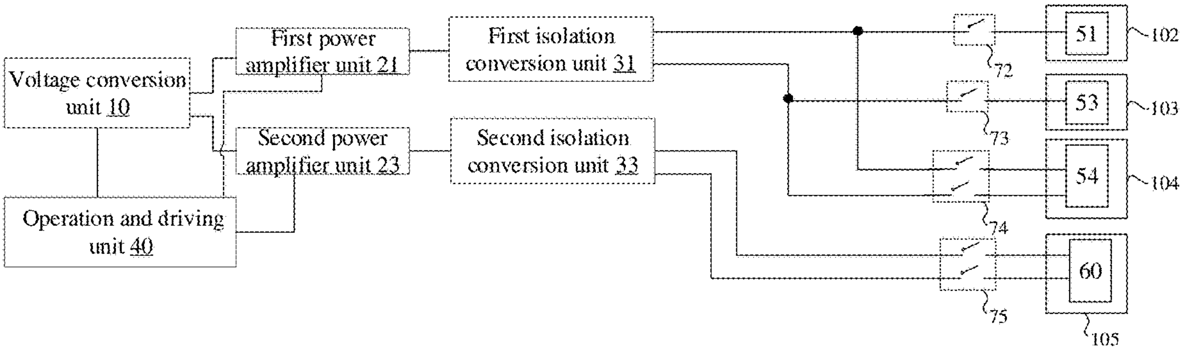
FIG. 19 is a structural diagram of an integrated surgical system according to an embodiment.

In some embodiments, referring to FIG. 19, the first group of mechanical insertion ports 101 includes a mono-pole mechanical insertion port 102, a neutral-pole mechanical insertion port 103, and a bi-pole mechanical insertion port 104; the first group of switches 71 includes a first group of sub-switches 72, a second group of sub-switches 73 and a third group of sub-switches 74; the first group of sub-switches 72 are configured to connect and disconnect an energy delivery from the isolation conversion unit 30 to the mono-pole terminal 51, the second group of sub-switches 73 are configured to connect and disconnect an energy delivery from the isolation conversion unit 30 to the neutral-pole terminal 53, and the third group of sub-switches 74 are configured to connect and disconnect an energy delivery from the isolation conversion unit 30 to the bi-pole terminal 54.

When the surgical instrument is inserted into the mono-pole mechanical insertion port 102, and the trigger key at the surgical instrument is triggered, the operation and driving unit 40 controls the first group of sub-switches 72 to be switched on, so as to deliver energy to the mono-pole electrosurgical knife through the voltage conversion unit 10, the first power amplification unit 21 and the isolation conversion unit 30, for example, the first isolation conversion unit 31.

When the surgical instrument is inserted into the neutral-pole mechanical insertion port 103, and the trigger key at the surgical instrument is triggered, the operation and driving unit 40 controls the second group of sub-switches 73 to be switched on, so as to deliver energy to the neutral-pole electrosurgical knife through the voltage conversion unit 10, the first power amplification unit 21 and the isolation conversion unit 30, for example, the first isolation conversion unit 31.

When the surgical instrument is inserted into the bi-pole mechanical insertion port 104, and the trigger key at the surgical instrument is triggered, the operation and driving unit 40 controls the third group of sub-switches 74 to be switched on, so as to deliver energy to the bi-pole electrosurgical knife through the voltage conversion unit 10, the first power amplification unit 21 and the isolation conversion unit 30, such as the first isolation conversion unit 31.

Figure 20:
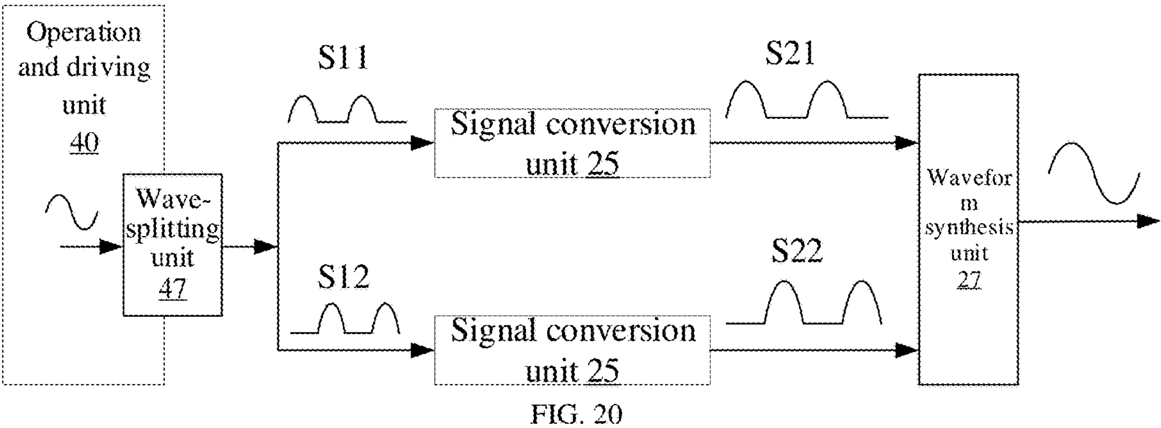
FIG. 20 is a structural diagram of a second power amplifier unit according to an embodiment.

Referring to FIG. 20, at least two paths of wave-split signals are wave-split by the operation and driving unit 40 through the wave-splitting unit 47, for example, sinusoidal-shaped chopping signals S11 and S12 (or a half-wave or other form of waveform, which is only used as an example description herein), and then signals S11 and S12 are converted (such as amplified) by the second power amplification unit 23, so as to obtain signals S21 and S22, which are synthesised to obtain a target waveform signal (for example, a sine-wave signal). The obtained target waveform signal (for example, a sine-wave signal) has a certain degree of distortion in its waveform during the wave-splitting, synthesis, and conversion, which results in that the obtained target waveform has a certain crossover distortion. On the one hand, there is a certain lag in correcting this distortion through software, and on the other hand, it is necessary to modify the waveform of the original third analog signal, that is, to modify, through feedback, the third analog signal waveform generated by the waveform generator 43 and the digital-analog conversion unit 45, which is unfavourable for the use of surgical devices (or surgical instruments, such as ultrasonic knife and electrosurgical knife mentioned in this disclosure).

In some embodiments, by introducing hardware feedback, the second power amplifier unit 23 finally outputs a desired target waveform signal, for example, a desired sine-wave signal, which may typically be a complete sine-wave signal. There is no or almost no crossover distortion, the waveform distortion does not need to be corrected to achieve a relatively ideal result, and this can be implemented by means of a hardware circuit, and has a lower cost, which is described in detail below.

In some embodiments, referring to FIG. 21 (*a*) or FIG. 22 (*a*), the second power amplifier unit 23 includes a signal conversion unit 25, a hardware feedback unit 26, and a waveform synthesis unit 27, which are described in detail below.

In some embodiments, a number of the signal conversion unit 25 is the same as a number of paths of the wave-split signals, and each signal conversion unit 25 is configured to receive one path of the wave-split signal for converting the wave-split signal and then output the converted wave-split wave. The waveform synthesis unit 27 is configured to receive and synthesize an output of each signal conversion unit 25 into one path of a sine-wave signal, and then output the synthesised sine-wave signal; and the synthesised output is used as the output of the second power amplification unit 23, so that the output of the waveform synthesis unit 27 is the target waveform signal.

In some embodiments, the signal conversion unit 25 is configured to convert the wave-split signal, including but not limited to signal amplification.

The introduction of the hardware feedback unit 26 is to enable the target waveform signal, which is outputted by the waveform synthesis unit 27, to be a desired target waveform signal, for example, a desired sine-wave signal. That is, the hardware feedback unit 26 is configured to feedback a signal received by an input terminal of the hardware feedback unit 26 to an output terminal of the hardware feedback unit 26, so that the target waveform signal, which is outputted by the waveform synthesis unit 27, is a desired target waveform signal, and the desired sine-wave signal is used to be provided to the energy output port 100.

Figure 21A:
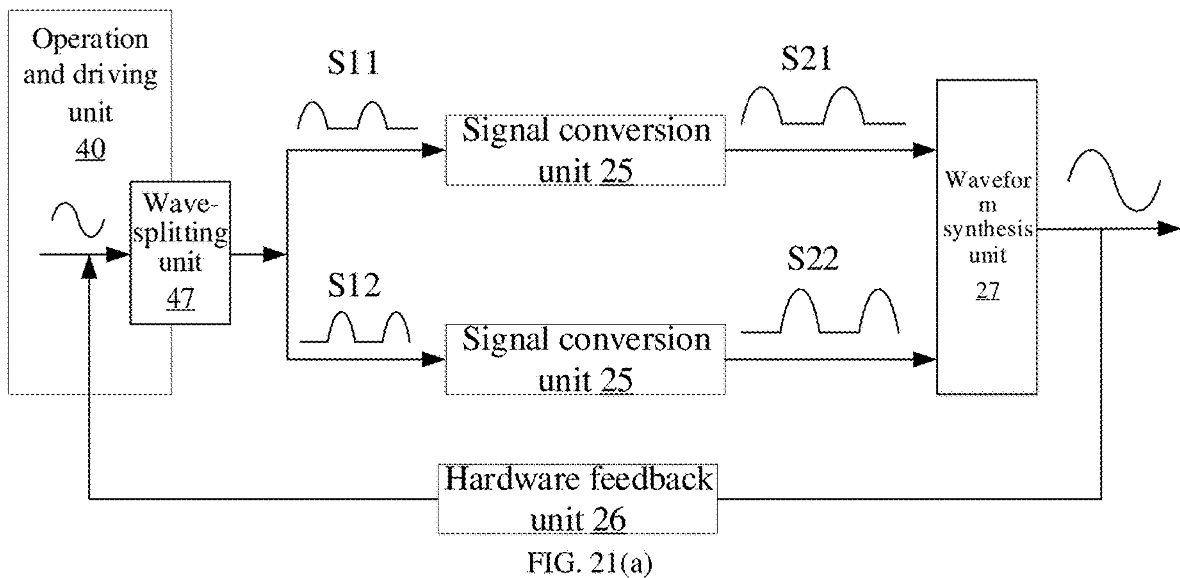
FIG. 21 (*a*) and FIG. 21 (*b*) are structural diagrams of a second power amplifier unit according to two embodiments.
Figure 21B:
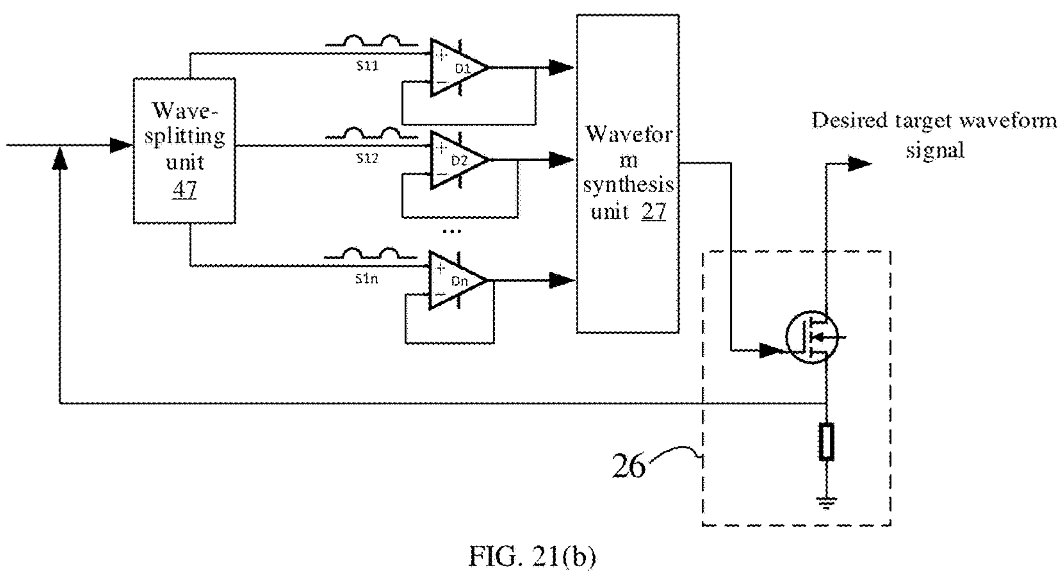

In some embodiments, referring to FIG. 21 (*a*), one hardware feedback unit 26 exists, an input terminal of the hardware feedback unit 26 is connected with an output terminal of the waveform synthesis unit 27, and an output terminal of the hardware feedback unit 26 is connected with an input terminal of the wave-splitting unit 47.

In some embodiments, referring to FIG. 21 (*b*), it is an example of the second power amplifier unit 23, wherein the signal conversion unit 25 may include an operational amplifier, for example, operational amplifiers D1 to Dn in the figure, wherein n is a serial number; and the hardware feedback unit 26 includes a transistor and a resistor.

In some embodiments, referring to FIG. 22 (*a*), a number of the hardware feedback units 26 is the same as the number of the signal conversion units 25, each hardware feedback unit 26 corresponds to one signal conversion unit 25, an input terminal of each hardware feedback unit 26 is connected with an output terminal of a corresponding signal conversion unit 25, and an output terminal of each hardware feedback unit 26 is connected with an input terminal of the corresponding signal conversion unit 25. In some embodiments, the hardware feedback unit 26 is configured to enable an output of the corresponding signal conversion unit 25 to accord with expectation, so as to further enable a target waveform signal, which is outputted by the waveform synthesis unit 27, to be a desired waveform signal.

In some embodiments, referring to FIG. 22 (*b*) or FIG. 22 (*c*), it is an example of the second power amplifier unit 23, wherein the signal conversion unit 25 may include an operational amplifier, for example, operational amplifiers D1 to Dn in the figure, wherein n is a serial number; and the hardware feedback unit 26 includes a transistor and a resistor. In some embodiments, the hardware feedback unit 26 is introduced to perform sampling and recognition process on the output signal of the signal conversion unit 25, and then feedback this output signal to the signal conversion unit 25, so that the signal conversion unit 25 compares the output signal with the corresponding inputted wave-split signal, and adjusts from its own output signal through continuous feedback adjustments.

In some embodiments, the hardware feedback unit 26 includes one or more of a power amplifier circuit, a resistor, a capacitor, an inductor, a diode, and a transistor.

It should be noted that the wave-split signal and the target waveform signal are exemplarily drawn in FIG. 21 (*a*), FIG. 21 (*b*), FIG. 22 (*a*), FIG. 22 (*b*), and FIG. 22 (*c*), but this is merely an example and does not indicate that the wave-split signal and the target waveform signal can only be such. In some embodiments, the target waveform signal is a sine-wave signal, and the desired target waveform signal is a desired sine-wave signal, for example, a complete sine-wave signal, so that a plurality of complete sine-wave signals constitute a periodic signal of the sine-wave signal.

The description has been made with reference to various exemplary embodiments herein. However, those skilled in the art recognize that changes and modifications can be made to the exemplary embodiments without departing from the scope herein. For example, various operation steps and components for performing operation steps may be implemented in different ways according to a specific application or considering any number of cost functions associated with the operation of the system (for example, one or more steps may be deleted, modified, or incorporated into other steps). Although the principles herein have been shown in various embodiments, many modifications of structures, arrangements, proportions, elements, materials, and components particularly suitable for the specific environmental and operational requirements may be used without departing from the principles and scope of this disclosure. The above modifications and other changes or amendments will be included in the scope of this disclosure. The foregoing specific description has been described with reference to various embodiments. However, those skilled in the art will recognize that various modifications and changes can be made without departing from the scope of this disclosure. Therefore, consideration of this disclosure will be in an illustrative rather than a restrictive sense, and all such modifications will be included within the scope thereof. Also, the advantages of various embodiments, other advantages, and the solutions to problems have been described above. However, the benefits, advantages, solutions to problems, and any elements that can produce these, or solutions that make them more explicit, should not be interpreted as critical, necessary, or essential. The term "including", and any other variants thereof used herein are non-exclusive, so that the process, method, document, or device that includes a list of elements includes not only these elements, but also other elements that are not explicitly listed or do not belong to the process, method, system, document, or device. Furthermore, the term "coupling" and any other variations thereof used herein refer to physical connection, electrical connection, magnetic connection, optical connection, communicational connection, functional connection, and/or any other connection.

Those skilled in the art can recognize that many changes may be made to the details of the above-described embodiments without departing from the underlying principles of this disclosure. Accordingly, the scope of this disclosure should be determined only by the claims.

What is claimed is:

1. An integrated surgical system, comprising a voltage conversion unit, a full-bridge power amplifier circuit, a linear power amplifier circuit, a first isolation conversion unit, a second isolation conversion unit, an operation and driving unit, a user input unit, a sampling unit, an output port for an electrosurgical knife, and an output port for an ultrasonic knife; wherein:

the output port for the electrosurgical knife is configured to deliver energy to the electrosurgical knife; the output port for the ultrasonic knife is configured to deliver energy to the ultrasonic knife;

the voltage conversion unit is configured to convert an input voltage into a DC voltage which drives the full-bridge power amplifier circuit or into a DC voltage which is delivered to the linear power amplifier circuit, according to a first control signal;

the full-bridge power amplifier circuit is configured to convert the DC voltage, which is outputted by the voltage conversion unit, into an AC voltage, according to a second control signal; wherein the first isolation conversion unit is configured to filter the AC voltage into a sine-wave voltage, perform resonance, isolation and conversion on the sine-wave voltage, and then deliver the sine-wave voltage to the output port for the electrosurgical knife for delivering energy to the electrosurgical knife;

the linear power amplifier circuit is configured to receive the DC voltage delivered from the voltage conversion unit, and convert a third signal into a sine-wave signal, wherein the third signal comprises two paths of a driving current signal; the second isolation conversion unit is configured to perform isolation and conversion on the sine-wave signal, and then deliver the sine-wave signal to the output port for the ultrasonic knife for delivering energy to the ultrasonic knife; and the sampling unit is configured to sample an input or an output of the first isolation conversion unit, so as to obtain a first sampled electrical signal; the sampling unit is further configured to sample an input or an output of the second isolation conversion unit, so as to obtain a second sampled electrical signal;

the user input unit is configured to receive a control parameter, which is inputted by a user; and the operation and driving unit is configured to generate the first control signal, the second control signal, and the third signal, according to the control parameter; wherein the operation and driving unit is further configured to adjust the first control signal and/or the second control signal according to the first sampled electrical signal, and to adjust the third signal according to the second sampled electrical signal.

2. An integrated surgical system, comprising a voltage conversion unit, a first power amplifier unit, a second power amplifier unit, an isolation conversion unit, an operation and driving unit, an output port for an electrosurgical knife, and an output port for an ultrasonic knife; wherein the output port for the electrosurgical knife is configured to deliver energy to the electrosurgical knife; the output port for the ultrasonic knife is configured to deliver energy to the ultrasonic knife;

the voltage conversion unit is configured to convert an input voltage into a DC voltage which drives the first power amplifier unit or into a DC voltage which is delivered to the second power amplifier unit, according to a first control signal;

the first power amplifier unit is configured to convert the DC voltage, which is outputted by the voltage conversion unit, into an AC voltage, and amplify the AC voltage, according to a second control signal; wherein the isolation conversion unit is configured to perform isolation and conversion on the amplified AC voltage, which is outputted by the first power amplifier unit, and then deliver the amplified AC voltage to the output port for the electrosurgical knife for delivering energy to the electrosurgical knife;

the second power amplifier unit is configured to receive the DC voltage delivered from the voltage conversion unit, amplify a third signal and output the amplified third signal; wherein the isolation conversion unit is further configured to perform isolation and conversion on an output of the second power amplifier unit, and then deliver said output to the output port for the ultrasonic knife for delivering energy to the ultrasonic knife; and the operation and driving unit is configured to generate the first control signal, the second control signal, and the third signal.

3. The integrated surgical system according to claim 2, wherein, the isolation conversion unit comprises a first isolation conversion unit and a second isolation conversion unit; the first isolation conversion unit is configured to perform isolation and conversion on an output of the first power amplifier unit, and then deliver said output to the output port for the electrosurgical knife;

the second isolation conversion unit is configured to perform isolation and conversion on the output of the second power amplifier unit, and then deliver said output to the output port for the ultrasonic knife;

the integrated surgical system further comprises a sampling unit; the sampling unit is configured to sample an input or an output of the first isolation conversion unit, so as to obtain a first sampled electrical signal; the sampling unit is further configured to sample an input or an output of the second isolation conversion unit, so as to obtain a second sampled electrical signal; and the operation and driving unit is further configured to adjust the first control signal and/or the second control signal according to the first sampled electrical signal, and to adjust the third signal according to the second sampled electrical signal.

4. The integrated surgical system according to claim 2, wherein, the isolation conversion unit comprises a first isolation conversion unit, which is configured to perform isolation and conversion on an output of the first power amplifier unit, and then deliver said output to the output port for the electrosurgical knife; the first isolation conversion unit comprises at least one of a series-parallel resonant circuit, a common-mode filter circuit, and a turning-off absorption circuit;

the series-parallel resonant circuit is configured to filter the output of the first power amplifier unit;

the common-mode filter circuit is configured to filter a common-mode signal out of the output of the first power amplifier unit; and the turning-off absorption circuit is configured to absorb oscillation after the first power amplifier unit is turned off.

5. The integrated surgical system according to claim 2, wherein, the first power amplifier unit is a full-bridge power amplifier circuit, an LC series circuit is connected between two output terminals of the full-bridge power amplifier circuit;

the second power amplifier unit is a linear power amplifier circuit; and/or the integrated surgical system further comprises an impedance matching circuit, which is connected between the second power amplifier unit and the isolation conversion unit, and configured to perform impedance matching.

6. The integrated surgical system according to claim 2, wherein, the operation and driving unit comprises a processor, a waveform generator, a digital-to-analog conversion unit, and a wave-splitting unit;

the processor is configured to generate the first control signal;

the processor is further configured to control the waveform generator to generate a second digital signal waveform as the second control signal; and the processor is further configured to control the waveform generator to generate a third digital signal waveform; the digital-to-analog conversion unit is configured to convert the third digital signal waveform into a third analog signal waveform, and the wave-splitting unit is configured to wave-split the third analog signal waveform to obtain the third signal.

7. The integrated surgical system according to claim 2, further comprising a user input unit configured to receive a control parameter which is inputted by a user; wherein the operation and driving unit is further configured to generate at least one of the first control signal, the second control signal, and the third signal, at least according to the control parameter.

8. The integrated surgical system according to claim 2, wherein the output port for the electrosurgical knife comprises a mono-pole terminal, a neutral-pole terminal, and a bi-pole terminal.

9. The integrated surgical system according to claim 8, further comprising a switch component, wherein the switch component comprises a first group of switches and a second group of switches; the first group of switches are configured to connect and disconnect an energy delivery from the isolation conversion unit to the output port for the electrosurgical knife; and the second group of switches are configured to connect and disconnect an energy delivery from the isolation conversion unit to the output port for the ultrasonic knife.

10. The integrated surgical system according to claim 9, wherein, the output port for the electrosurgical knife and the output port for the ultrasonic knife share a mechanical insertion port; when a surgical instrument is inserted into the mechanical insertion port, the operation and driving unit is further configured to identify a type of an inserted surgical instrument through the mechanical insertion port; the surgical instrument at least comprises two types, one type is an ultrasonic knife, and the other type is an electrosurgical knife; and the surgical instrument is provided with a trigger key;

the operation and driving unit is further configured to control the first group of switches to be switched on, so as to deliver energy to the electrosurgical knife through the voltage conversion unit, the first power amplifier unit and the isolation conversion unit, when the trigger key is triggered and the type of the surgical instrument is currently identified as the electrosurgical knife; and the operation and driving unit is further configured to control the second group of switches to be switched on, so as to deliver energy to the ultrasonic knife through the voltage conversion unit, the second power amplifier unit and the isolation conversion unit, when the trigger key is triggered and the type of the surgical instrument is currently identified as the ultrasonic knife.

11. The integrated surgical system according to claim 10, wherein, the type of the electrosurgical knife comprises at least three types, a first type is a mono-pole electrosurgical knife, a second type is a neutral-pole electrosurgical knife, and a third type is a bi-pole electrosurgical knife; the first group of switches comprise a first group of sub-switches, a second group of sub-switches, and a third group of sub-switches; the first group of sub-switches are configured to connect and disconnect an energy delivery from the isolation conversion unit to the mono-pole terminal; the second group of sub-switches are configured to connect and disconnect an energy delivery from the isolation conversion unit to the neutral-pole terminal; and the third group of sub-switches are configured to connect and disconnect an energy delivery from the isolation conversion unit to the bi-pole terminal;

in order to control the first group of switches to be switched on, so as to deliver energy to the electrosurgical knife through the voltage conversion unit, the first power amplifier unit and the isolation conversion unit, when the trigger key is triggered and the type of the surgical instrument is currently identified as the electrosurgical knife; and the operation and driving unit is further configured to:

control the first group of sub-switches to be switched on, so as to deliver energy to the mono-pole electrosurgical knife through the voltage conversion unit, the first power amplifier unit and the isolation conversion unit, when the trigger key is triggered and the type of the surgical instrument is currently identified as the mono-pole electrosurgical knife;

control the second group of sub-switches to be switched on, so as to deliver energy to the neutral-pole electrosurgical knife through the voltage conversion unit, the first power amplifier unit and the isolation conversion unit, when the trigger key is triggered and the type of the surgical instrument is currently identified as the neutral-pole electrosurgical knife; and control the third group of sub-switches to be switched on, so as to deliver energy to the bi-pole electrosurgical knife through the voltage conversion unit, the first power amplifier unit and the isolation conversion unit, when the trigger key is triggered and the type of the surgical instrument is currently identified as the bi-pole electrosurgical knife.

12. The integrated surgical system according to claim 9, wherein, the output port for the electrosurgical knife and the output port for the ultrasonic knife share a same mechanical insertion port; a mechanical insertion port is capable of being inserted by an integrated surgical instrument, and the integrated surgical instrument is provided with a trigger key;

the operation and driving unit is further configured to obtain a working mode of an inserted integrated surgical instrument, the working mode of the integrated surgical instrument at least comprises two modes, a mode relating to the electrosurgical knife and a mode relating to the ultrasonic knife;

the operation and driving unit is further configured to control the first group of switches to be switched on, so as to deliver energy to the integrated surgical instrument through the voltage conversion unit, the first power amplifier unit and the isolation conversion unit, when the trigger key is triggered and the integrated surgical instrument currently works in the mode relating to the electrosurgical knife; and the operation and driving unit is further configured to control the second group of switches to be switched on, so as to deliver energy to the integrated surgical instrument through the voltage conversion unit, the second power amplifier unit, and the isolation conversion unit, when the trigger key is triggered and the integrated surgical instrument currently works in the mode relating to the ultrasonic knife.

13. The integrated surgical system according to claim 12, wherein, the mode relating to the electrosurgical knife comprises at least three modes, a first mode relating to a mono-pole electrosurgical knife, a second mode relating to a neutral-pole electrosurgical knife, and a third mode relating to a bi-pole electrosurgical knife;

the first group of switches comprise a first group of sub-switches, a second group of sub-switches, and a third group of sub-switches; the first group of sub-switches are configured to connect and disconnect an energy delivery from the isolation conversion unit to the mono-pole terminal; the second group of sub-switches are configured to connect and disconnect an energy delivery from the isolation conversion unit to the neutral-pole terminal; the third group of sub-switches are configured to connect and disconnect an energy delivery from the isolation conversion unit to the bi-pole terminal;

the operation and driving unit is further configured to control the first group of sub-switches to be switched on, so as to deliver energy to the integrated surgical instrument through the voltage conversion unit, the first power amplifier unit and the isolation conversion unit, when the trigger key is triggered and the integrated surgical instrument currently works in the mode relating to the mono-pole electrosurgical knife;

the operation and driving unit is further configured to control the second group of sub-switches to be switched on, so as to deliver energy to the integrated surgical instrument through the voltage conversion unit, the first power amplifier unit and the isolation conversion unit, when the trigger key is triggered and the integrated surgical instrument currently works in the mode relating to the neutral-pole electrosurgical knife; and the operation and driving unit is further configured to control the third group of sub-switches to be switched on, so as to deliver energy to the integrated surgical instrument through the voltage conversion unit, the first power amplifier unit and the isolation conversion unit, when the trigger key is triggered and the integrated surgical instrument currently works in the mode relating to the bi-pole electrosurgical knife.

14. The integrated surgical system according to claim 12, further comprising a switch component which is configured to switch between working modes of the integrated surgical instrument; wherein, the switch component comprises a foot switch.

15. The integrated surgical system according to claim 9, wherein, the output port for the electrosurgical knife is provided with a first group of mechanical insertion ports, and the output port for the ultrasonic knife is provided with a second group of mechanical insertion ports;

the operation and driving unit is further configured to control the first group of switches to be switched on, so as to deliver energy to the electrosurgical knife through the voltage conversion unit, the first power amplifier unit and the isolation conversion unit, when a surgical instrument is inserted into the first group of mechanical insertion ports and a trigger key at said surgical instrument is triggered; and the operation and driving unit is further configured to control the second group of switches to be switched on, so as to deliver energy to the ultrasonic knife through the voltage conversion unit, the second power amplifier unit and the isolation conversion unit, when a surgical instrument is inserted into the second group of mechanical insertion ports and a trigger key at said surgical instrument is triggered.

16. The integrated surgical system according to claim 15, wherein, the first group of mechanical insertion ports comprise a mono-pole mechanical insertion port, a neutral-pole mechanical insertion port, and a bi-pole mechanical insertion port;

the first group of switches comprise a first group of sub-switches, a second group of sub-switches, and a third group of sub-switches; the first group of sub-switches are configured to connect and disconnect an energy delivery from the isolation conversion unit to the mono-pole terminal; the second group of sub-switches are configured to connect and disconnect an energy delivery from the isolation conversion unit to the neutral-pole terminal; the third group of sub-switches are configured to connect and disconnect an energy delivery from the isolation conversion unit to the bi-pole terminal;

in order to control the first group of switches to be switched on, so as to deliver energy to the electrosurgical knife through the voltage conversion unit, the first power amplifier unit and the isolation conversion unit, when a surgical instrument is inserted into the first group of mechanical insertion ports and a trigger key at the surgical instrument is triggered; the operation and driving unit is further configured to:

control the first group of sub-switches to be switched on, so as to deliver energy to the mono-pole terminal through the voltage conversion unit, the first power amplifier unit and the isolation conversion unit, when a surgical instrument is inserted into the mono-pole mechanical insertion port and a trigger key at said surgical instrument is triggered;

control the second group of sub-switches to be switched on, so as to deliver energy to the neutral-pole terminal through the voltage conversion unit, the first power amplifier unit and the isolation conversion unit, when a surgical instrument is inserted into the neutral-pole mechanical insertion port and a trigger key at said surgical instrument is triggered; and control the third group of sub-switches to be switched on, so as to deliver energy to the bi-pole terminal through the voltage conversion unit, the first power amplifier unit and the isolation conversion unit, when a surgical instrument is inserted into the bi-pole mechanical insertion port and a trigger key at said surgical instrument is triggered.

17. The integrated surgical system according to claim 2, wherein, the operation and driving unit comprises a wave-splitting unit; the operation and driving unit is further configured to generate a third analog signal waveform, which is wave-split into at least two paths of a wave-split wave signal when passing through the wave-splitting unit, and the wave-split wave signal is used as the third signal;

the second power amplifier unit comprises a signal conversion unit, a hardware feedback unit, and a waveform synthesis unit; a number of the signal conversion unit is same as a number of paths of the wave-split wave signal, each signal conversion unit is configured to receive one path of the wave-split wave signal, amplify said path of the wave-split wave signal and then output the amplified path of the wave-split wave signal; the waveform synthesis unit is configured to receive and synthesize an output of each signal conversion unit into one path of a sine-wave signal, and then output said sine-wave signal;

when one hardware feedback unit exists, an input terminal of said hardware feedback unit is connected with an output terminal of the waveform synthesis unit, and an output terminal of said hardware feedback unit is connected with an input terminal of the wave-splitting unit; or when a number of the hardware feedback unit is same as the number of the signal conversion unit, each hardware feedback unit corresponds to one signal conversion unit, an input terminal of each hardware feedback unit is connected with an output terminal of a corresponding signal conversion unit, and an output terminal of said each hardware feedback unit is connected with an input terminal of said corresponding signal conversion unit; and the hardware feedback unit is configured to feedback a signal, which is received by its input terminal, to its output terminal, so as to enable said sine-wave signal, which is outputted by the waveform synthesis unit, to be a desired sine-wave signal.

18. The integrated surgical system according to claim 17, wherein, when the number of the hardware feedback unit is the same as the number of the signal conversion unit, the hardware feedback unit is configured to enable a target waveform signal, which is outputted by the waveform synthesis unit, to be the desired sine-wave signal.

19. The integrated surgical system according to claim 2, wherein, the voltage conversion unit comprises a step-up circuit, which is configured to receive a negative DC voltage, and convert the negative DC voltage into a positive DC voltage according to the first control signal;

the step-up circuit comprises one or more step-up branches; each step-up branch comprises an energy conversion inductor, a charging switch, and a discharging switch; the charging switch and the discharging switch are configured to be switched on and off according to the first control signal, so as to charge and discharge the energy conversion inductor for voltage step-up; and one terminal of the energy conversion inductor is grounded, the other terminal of the energy conversion inductor is connected with a voltage input terminal of the step-up circuit through the charging switch, and the voltage input terminal of the step-up circuit is configured to receive the negative DC voltage; the other terminal of the energy conversion inductor, which terminal is not grounded, is further connected with a voltage output terminal of the step-up circuit through the discharging switch, and the voltage output terminal of the step-up circuit is configured to output the positive DC voltage.

20. The integrated surgical system according to claim 2, wherein, the voltage conversion unit is configured to receive a negative voltage and output an adjustable positive voltage; the voltage conversion unit comprises one inductive element and two switch elements; one terminal of the inductive element and one terminal of each of the two switch elements are connected together, the other terminal of the inductive element is grounded, the other terminals of the two switch elements are respectively used as an input terminal and an output terminal, and respective switching-on times of the two switch elements are staggered, so as to realize a voltage conversion function.

* * * * *